(12) United States Patent
Hakim et al.

(10) Patent No.: US 10,994,109 B2
(45) Date of Patent: May 4, 2021

(54) CONNECTABLE CATHETER

(71) Applicant: UROGEN PHARMA LTD., Ra'anana (IL)

(72) Inventors: Gil Hakim, Ra'anana (IL); Yosh Dollberg, Raanana (IL); Nadav Malchi, Ra'anana (IL)

(73) Assignee: Urogen Pharma Ltd., Ra'anana (IL)

( * ) Notice: Subject to any disclaimer, the term of this patent is extended or adjusted under 35 U.S.C. 154(b) by 0 days.

(21) Appl. No.: 15/322,044

(22) PCT Filed: Jun. 25, 2015

(86) PCT No.: PCT/IL2015/050662
§ 371 (c)(1),
(2) Date: Dec. 23, 2016

(87) PCT Pub. No.: WO2015/198333
PCT Pub. Date: Dec. 30, 2015

(65) Prior Publication Data
US 2017/0136222 A1  May 18, 2017

Related U.S. Application Data

(60) Provisional application No. 62/017,967, filed on Jun. 27, 2014.

(51) Int. Cl.
*A61F 2/04* (2013.01)
*A61F 2/82* (2013.01)
(Continued)

(52) U.S. Cl.
CPC ............. *A61M 27/008* (2013.01); *A61F 2/04* (2013.01); *A61F 2/82* (2013.01); *A61F 2/94* (2013.01);
(Continued)

(58) Field of Classification Search
CPC ........ A61M 5/00; A61M 31/00; A61M 39/10; A61M 27/00; A61M 25/01
See application file for complete search history.

(56) References Cited

U.S. PATENT DOCUMENTS 4,790,809 A    12/1988  Kuntz
4,932,959 A *  6/1990  Horzewski ............ A61M 25/01
                                                        604/96.01
(Continued)

FOREIGN PATENT DOCUMENTS

WO    2013134758 A1   9/2013

OTHER PUBLICATIONS

International Search Report for PCT Application No. PCT/IL2015/050662, dated Oct. 29, 2015.

*Primary Examiner* — Yashita Sharma
(74) *Attorney, Agent, or Firm* — Greenberg Traurig, LLP

(57) ABSTRACT

There are provided a connectable catheter system, device and methods of use thereof. The connectable catheter system, comprising: an intermediary catheter comprising an external section and a tip section, the tip section is configured to be inserted into a body of a subject; and a reconnectable indwelling stent comprising a connecting section and a target section, the target section being configured to be located within a body of the subject, wherein the connecting section of the reconnectable indwelling stent is configured to reversibly connect, within the subject body, to the tip section of the intermediary catheter to form a continuous conduit between the intermediary catheter and the reconnectable indwelling stent.

11 Claims, 15 Drawing Sheets

(51) Int. Cl.
  *A61F 2/94* (2013.01)
  *A61M 25/01* (2006.01)
  *A61M 25/02* (2006.01)
  *A61M 27/00* (2006.01)
  *A61M 31/00* (2006.01)
  *A61M 39/10* (2006.01)
  *A61M 25/04* (2006.01)
  *A61M 25/10* (2013.01)

(52) U.S. Cl.
  CPC .... *A61M 25/0102* (2013.01); *A61M 25/0136* (2013.01); *A61M 25/04* (2013.01); *A61M 31/00* (2013.01); *A61M 39/10* (2013.01); A61F 2002/047 (2013.01); A61F 2002/048 (2013.01); A61M 25/0108 (2013.01); A61M 25/0127 (2013.01); A61M 25/1011 (2013.01); A61M 2025/0293 (2013.01); A61M 2025/105 (2013.01)

(56) References Cited

U.S. PATENT DOCUMENTS

| | | | | |
|---|---|---|---|---|
| 5,507,731 A | * | 4/1996 | Hernandez | A61M 25/00 604/264 |
| 5,941,869 A | * | 8/1999 | Patterson | A61B 17/3207 604/22 |
| 2015/0088098 A1 | * | 3/2015 | Lane | A61M 3/0279 604/514 |

* cited by examiner

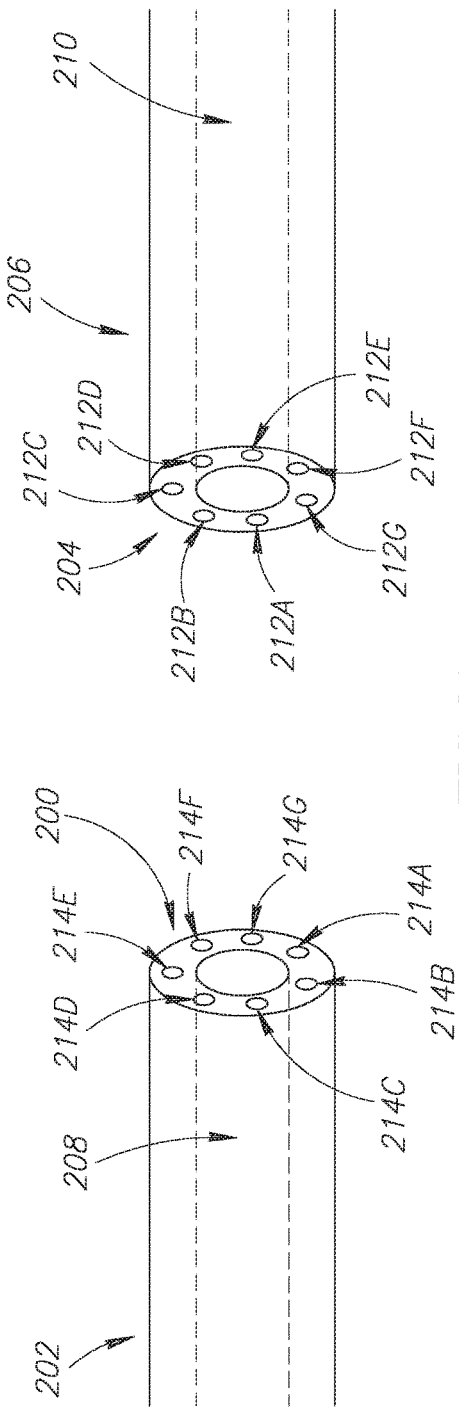
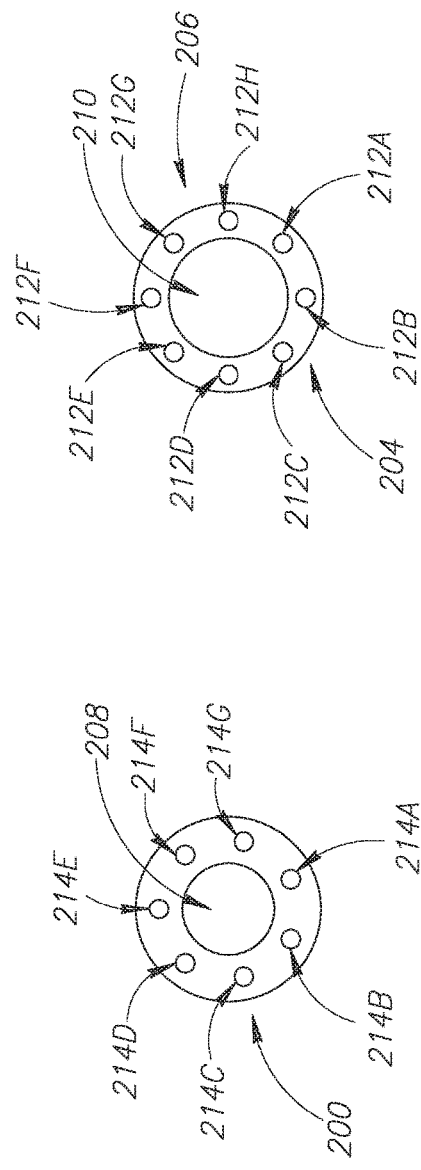
FIG.6A
FIG.6B

CONNECTABLE CATHETER

This application is a US 371 National Entry of International PCT Application No. PCT/IL2015/050662, filed Jun. 25, 2015, which claims priority to U.S. Provisional Patent Application Ser. No. 62/017,967, filed on Jun. 27, 2017, the entire contents of which are incorporated by reference in their entirety.

FIELD OF THE INVENTION

The present invention relates to a connectable catheter system, device and methods of use thereof, wherein the catheter is configured to connect within a subject body.

BACKGROUND OF THE INVENTION

In the field of medical devices, a catheter is in essence a tube that can be inserted into the body to transfer fluids into and out of a human. The catheter's size, shape and composition may be adjusted for its use, for example, for cardiovascular, urological, gastrointestinal, neurovascular, and ophthalmic applications. Catheters can be inserted into a body cavity, duct, or vessel. Functionally, they may allow drainage, administration of fluids, access by surgical instruments, and perform a wide variety of other medical procedures depending on the type of catheter. Depending on the application, a catheter is usually transiently inserted into the target organ and removed once the procedure is completed. A catheter that is left inside the body, either temporarily or permanently, is generally referred to as an indwelling catheter or stent.

Ureteral catheters, for example, are inserted through the meatus, through the bladder and ureter and advanced until the catheter extends from outside the body to the renal pelvis, for example, in order to deliver medications to the upper urinary tract. Due to severe risk of infection, ureteral catheters are mostly removed from the urinary tract immediately following the delivery of medication. If an additional installation of medication is required subsequently, an additional ureteral catheter is inserted for that purpose.

Ureteral stents (indwelling catheters) are deployed into the ureter and extend from the urinary bladder to the renal pelvis. They are used to dilate the ureter, for example, in order to facilitate the passage of urine and debris from the kidney and ureter to the bladder in cases of ureteral obstructions such as stones, strictures, edema, fistula, tumors, retro-peritoneal fibrosistumors, and hydronephrosis. Indications for use of a ureteral stent include such uses as: (I) as adjunct to such surgical procedures as extracorporeal shock wave lithotripsy (ESWL), percutaneous nephrolithotomy (PCNL), ureteroscopy, endopylometry, ureteral surgery, ureter injury, renal transplantation, upper tract urothelial carcinoma (UTUC) and conservative treatment of genitourinary fistulas in women.

A ureteral stent may be retained in the urinary tract for an extended period of time, such as several weeks or months. Ureteral catheters and stents alike may be positioned in the urinary tract using endoscopic techniques or percutaneously (stents only). The current standard procedure for the insertion of ureteral catheter uses a ureteroscope and X-Ray guidance and is performed on anesthetized patients. These conditions require the procedure to be performed in an operating room, thus increasing procedure cost and patient's morbidity.

Repeated insertion and removal of a catheter, in particular, indwelling catheter, such as ureteral catheters, entails repeated anesthesia and exposure to radiation of the patient, and increases the chances of damage to internal organs, such as uretrovesical valve (the orifice between the ureter and the bladder). Thus, reducing the number of such catheter insertions would dramatically reduce adverse effects for patients.

There is thus a need in the art for catheters that are connectable and that can specifically and securely connect within the subject body to/from a continuous catheter system, which does not require the repeated insertion of indwelling catheters into the subject's body.

SUMMARY

According to some embodiments, there is provided a connectable catheter system, device and methods of using the same. In some embodiments, the catheter systems disclosed herein may be used for various applications for delivery or removal of various substances to various target body parts, organs or cavities. In some embodiments, the connectable catheter system and devices disclosed herein include an internal, indwelling part (stent), which has already been pre-inserted into a desired target location/organ within a subject's body, and a removable, external, intermediary part (catheter), which is capable of specifically and safely connect to the indwelling part, within the subject body, to form a continuous catheter system capable of transferring fluids or other substances from/to the external location to/from an internal organ/cavity.

As detailed herein below, the systems, devices and methods disclosed herein are advantageous over currently used methods and catheter systems, as they can be used to complement the operation of an indwelling stent or catheter and allow minimizing the repetition of insertion procedures of internal, indwelling stents to the target organ/cavity and thereby dramatically reducing risks involved therewith (such as, anesthesia, infections and physical damage to internal organs) as well as and increasing safety of treatment and improving overall well-being of the subject. In addition, this can reduce the chance of tumor cell seeding, if a tumor develops in said organ/cavity.

In some embodiments, the systems, devices and methods disclosed herein are advantageous, as they allow the specific, accurate, safe and reversible connection of an indwelling stent that has been placed within the subject body (for example, at or in a target organ or cavity) and a main, intermediary catheter (which may be transiently inserted and removed from the subject body), wherein the connection is being made within the subject body, without the need for repeated insertions of the indwelling stent, which may be left in its internal location and reconnected at will to the intermediary catheter that may be transiently inserted as needed. In some embodiments, the connection that is being made within the subject body, does not require visual guidance.

According to some embodiments, there is thus provided a connectable catheter system comprising an intermediary catheter and an indwelling stent catheter. The intermediary catheter includes an external (proximal) section (end) and a tip (internal/distal) section (end) opposing thereto, the tip section is configured to be inserted into a body of a subject. The indwelling stent, configured to be located within the body of the subject, includes a connecting section (end) and a target section (end); wherein the connecting section of the indwelling stent is configured to reversibly connect, within the body of the subject, with the tip section of the intermediary catheter to form a continuous conduit (such as a continuous fluid passage) from the external section (end) of the intermediary catheter to the indwelling stent.

According to some embodiments, there is provided a connectable catheter system, comprising: an intermediary catheter comprising an external section and a tip section, the tip section is configured to be inserted into a body of a subject; and a reconnectable indwelling stent comprising a connecting section and a target section, the target section being configured to be located within a body of the subject, wherein the connecting section of the reconnectable indwelling stent is configured to reversibly connect, within the body, to the tip section of the intermediary catheter to form a continuous fluid conduit between the intermediary catheter and the reconnectable indwelling stent.

According to some embodiments, the connecting section of the reconnectable indwelling stent is configured to fit into an inner lumen of the tip section of the intermediary catheter.

In some embodiments, the inner lumen of the intermediary catheter may include a securing member configured to secure the connecting section of the reconnectable indwelling stent within the inner lumen of the tip section of the intermediary catheter. In some embodiments, the securing member may include a deployable securing member, vacuum ducts, a flexible plate, matching recesses in the connecting section of the reconnectable indwelling stent and the inner lumen of the tip section of the intermediary catheter, or any combination thereof. In some exemplary embodiments, the securing member may include one or more inflatable balloons, configured to be inflated within the inner lumen of the intermediary catheter. In some embodiments, the intermediary catheter may further include one or more inflating port(s) configured to inflate the one or more inflatable balloons.

In some embodiments, the securing member may be further configured to seal a fluid passage between the outer wall of the reconnectable indwelling stent and the inner wall of the intermediary catheter.

According to some embodiments, the intermediary catheter may further include a sealing member configured to seal a fluid passage between the outer wall of the reconnectable indwelling stent and the inner wall of the intermediary catheter. In some embodiments, the sealing member is configured to prevent fluid leakage between the intermediary catheter and indwelling stent. In some embodiments, the sealing member may prevent or overcome decoupling forces that may be exerted when the fluid provided is viscous.

In some embodiments, the system may further include a stylet removably insertable into the inner lumen of the intermediary catheter, the stylet includes, at a tip section thereof, an attachment member configured to capture and/or attach to the connecting section of the reconnectable indwelling stent, such that when the stylet is proximally retracted within the inner lumen of the intermediary catheter, the reconnectable indwelling stent is pulled into the inner lumen of the intermediary catheter. In some embodiments, the stylet's attachment member may include a magnet configured to attract the connecting section of the reconnectable indwelling stent. In some exemplary embodiments, the stylet's attachment member may include a magnet configured to attract a corresponding magnet that is located on the connecting section of the indwelling stent, and which is integrally formed therewith.

According to some embodiments, the connecting section of the indwelling stent may include a magnet or a component attractable by the stylet's magnet. That magnet or component attractable by the stylet's magnet may be configured to be placed or formed around the indwelling catheter lumen such that passage of fluids therethrough is enabled.

In some embodiments, the connecting section of the reconnectable indwelling stent may include a magnet or a component attractable by the stylet's magnet.

In some embodiments, the stylet's attachment member may include a loop, lasso, protrusion, pigtail, net, basket structure or any combination thereof. In some embodiments, the connecting section of the indwelling stent is fitted with a corresponding connection member that may be an integrated part of the stent luminal tube. In some embodiments, the connecting section of the reconnectable indwelling stent may include a loop, protrusion, lasso, pigtail or any combination thereof.

In some embodiments, the stylet may further include or be functionally associated with an indication unit configured to provide an indication of a connection between the attachment member of the stylet and the connecting section of the reconnectable indwelling stent.

In some embodiments, the reconnectable indwelling stent may include a stopper element at an outer wall thereof, wherein the stopper element may be located between the connecting section and the target section and wherein the stopper element is configured to limit the length (portion) of the reconnectable indwelling stent that can enter the inner lumen of the intermediary catheter.

In some embodiments, the system may further include a guide rod removably insertable into the inner lumen of the connectable catheter, the guide rod is configured to facilitate the penetration of the tip section of the intermediary catheter into the subject's body. In some embodiments, the guide rod is comprised with an a-traumatic tip and/or a flexible end-section.

In some embodiments, the guide rod may be further configured to remove the reconnectable indwelling stent from the intermediary catheter when pushed distally within the inner lumen of the connectable catheter.

In some embodiments, the intermediary catheter may further include a deployable anchoring element located at an outer wall thereof, the deployable anchoring element, when deployed, is configured to anchor the intermediary catheter in the subject's body.

In some embodiments, the intermediary catheter may further include opening(s) or administration port(s) for allowing the transfer of fluids and/or various devices (such as, guide-wires). In some embodiments, the intermediary catheter may include a one or more connector(s) and/or one or more administration port(s), such as, a medical substance administration port.

In some embodiments, the system may further include a control circuitry unit configured to provide an indication when the continuous fluid conduit is formed.

In some embodiments, the system may further include a vacuum source configured to create vacuum in the inner lumen of the intermediary catheter to secure the positioning of the reconnectable indwelling stent.

According to some embodiments, there is provided an intermediary catheter, comprising: an external section and a tip section, the tip section is configured to be inserted into a body of a subject; a securing member located at an inner lumen of the intermediary catheter, the securing member is configured to secure a connecting section of an reconnectable indwelling stent within the inner lumen of the tip section thereof and thereby to form a continuous fluid conduit between the inner lumen of the intermediary catheter and an inner lumen of the reconnectable indwelling stent.

In some embodiments, the securing member may include a deployable securing member, vacuum ducts, matching recesses in the connecting section of the reconnectable indwelling stent and the inner lumen of the tip section of the intermediary catheter, or combinations thereof. In some embodiments, the securing member comprises one or more inflatable balloons.

In some embodiments, the intermediary catheter may further include an inflating port configured to inflate the one or more inflatable balloons.

In some embodiments, the securing member may be further configured to seal a fluid passage between an outer wall of the reconnectable indwelling stent and the inner wall of the intermediary catheter. In some embodiments, the intermediary catheter may further include a sealing member configured to seal a fluid passage between the outer wall of the reconnectable indwelling stent and the inner wall of the intermediary catheter. In some embodiments, the intermediary catheter may further include a deployable anchoring element located at an outer wall thereof, the deployable anchoring element, when deployed, is configured to anchor the intermediary catheter in the subject's body. In some embodiments, the intermediary catheter may further include a one or more connectors(s) and/or one or more administration port(s), such as, a medical substance administration port.

In some embodiments, the intermediary catheter may be functionally associated with a control circuitry unit configured to provide an indication when the continuous fluid conduit is formed.

In some embodiments, the intermediary catheter may be functionally associated with a vacuum member configured to create vacuum in the inner lumen of the intermediary catheter to secure the positioning of the reconnectable indwelling stent.

According to some embodiments, there is provided a reconnectable indwelling stent comprising: a target section configured to be located within a subject's body cavity; a connecting section configured to reversibly connect, within the body, to a tip section of an intermediary catheter to form a continuous fluid conduit between the intermediary catheter and the reconnectable indwelling stent; and a main section located between said target section and said connecting section, wherein said connecting section is firmly attached to or integrally formed with the main section.

In some embodiments, the connecting section may include a magnet or a component attractable by a magnet. In some embodiments, the connecting section may include a loop, lasso, pigtail or any combination thereof.

In some embodiments, the reconnectable indwelling stent may further include a stopper element at an outer wall thereof, wherein the stopper element is located on the main section and wherein the stopper element is configured to limit the portion (length) of the reconnectable indwelling stent that can enter the inner lumen of the intermediary catheter.

In some embodiments, the reconnectable indwelling stent may further include one or more drainage holes at a wall thereof.

In some embodiments, the reconnectable indwelling stent may be configured to transfer fluids from the body cavity and/or to the body cavity after formation of the continuous fluid conduit.

According to some embodiments, there is provided a stylet for removable insertion into an inner lumen of an intermediary catheter, the stylet comprises, at a tip section thereof, an attachment member configured to attach, within a subject's body, to the connecting section of a reconnectable indwelling stent, such that when the stylet is proximally retracted within the inner lumen of the intermediary catheter, the reconnectable indwelling stent is pulled into the inner lumen of the intermediary catheter.

In some embodiments, the attachment member of the stylet may include a magnet or a component attractable by a magnet configured to attract the connecting section of the reconnectable indwelling stent.

In some embodiments, the stylet's tip section is flexible. In some embodiments, the stylet's tip section may include a shape memory material configured to obtain a bent configuration upon exiting a tip section of the intermediary catheter.

In some embodiments, the stylet's attachment member may include a loop, a lasso, a pigtail, a net, a basket structure, or any combination thereof.

According to some embodiments, there is provided a method of connecting a connectable catheter system, the method comprising: drawing a connecting section of a reconnectable indwelling stent into an inner lumen of the intermediary catheter; securing the connecting section of the reconnectable indwelling stent within the inner lumen of a tip section of the intermediary catheter, thereby forming a continuous fluid conduit between the inner lumen of the intermediary catheter and an inner lumen of the reconnectable indwelling stent; and utilizing a control circuitry unit, providing an indication when the continuous fluid conduit is formed.

In some embodiments, securing the connecting section of the reconnectable indwelling stent within the inner lumen of the tip section of the intermediary catheter may include deploying a securing member located at an inner lumen of the intermediary catheter.

In some embodiments, drawing (pulling) a connecting section of the reconnectable indwelling stent into the inner lumen of the intermediary catheter may be conducted by inserting a stylet into the inner lumen of the intermediary catheter, the stylet comprises, at a tip section thereof, an attachment member configured to attach to the connecting section of the reconnectable indwelling stent, such that when the stylet is proximally retracted within the inner lumen of the intermediary catheter, the reconnectable indwelling stent is pulled into the inner lumen of the intermediary catheter.

In some embodiments, the method may further include automatically providing, utilizing an indication unit, an indication when a connection between the attachment member of the stylet and the connecting section of the reconnectable indwelling stent is formed.

According to some embodiments, there is provided a method of treating cancer, the method comprising administering an anti-cancer drug to a subject in a need thereof, utilizing the connectable catheter system disclosed herein. In some embodiments, the anti-cancer drug is administered to a target organ/cavity. In some embodiments, the cancer is a urinary tract cancer.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 4A—prior to connection; FIG. 4B—after connection; FIG. 4C—after connection and insertion of the indwelling stent into the intermediary catheter;

FIG. 5A—prior to removal of stylet; FIG. 5B—after removal of stylet and formation of a continuous fluid conduit; FIG. 5C—prior to removal of stylet and prior to securing and/or sealing the connection; FIG. 5D—after removal of stylet and formation of a secured and sealed continuous fluid conduit between the indwelling stent and the intermediary catheter;

FIGS. 6A-D—schematic illustrations of exemplary means for approximating and/or connecting and/or securing the connection of the tip section of an intermediary catheter with the connecting section of the indwelling stent, according to some embodiments; FIGS. 6A-6B—connection with magnets; FIG. 6C—connection using a three dimensional basket structure; FIG. 6D—attachment and securing of the connection using vacuum ducts;

DETAILED DESCRIPTION

Figure 1A:
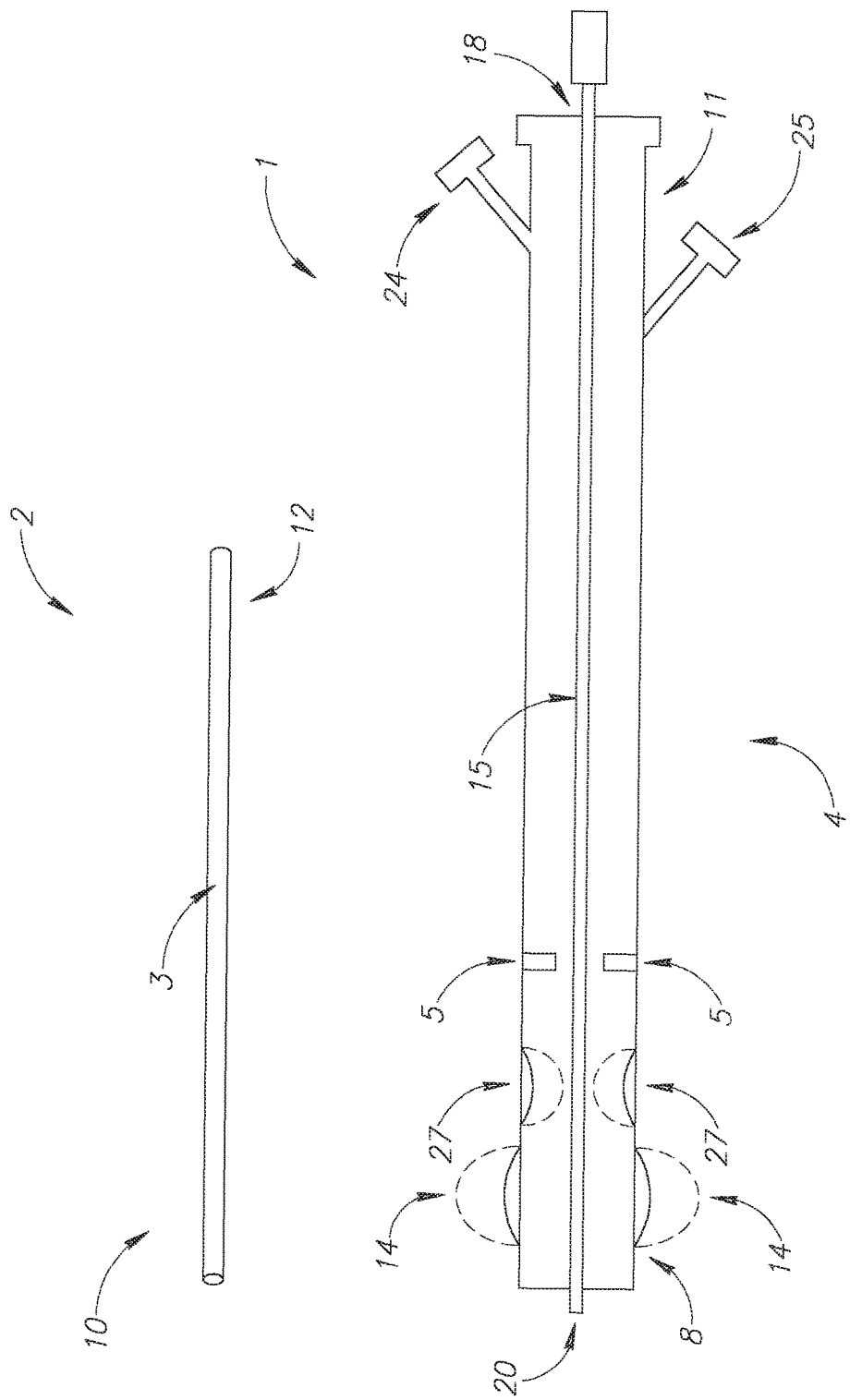
FIGS. 1A-B—Schematic perspective views of parts of a connectable catheter system, according to some embodiments.

According to some embodiments, there is provided an advantageous connectable catheter system and devices, configured to being connected within a body of a subject to form a continuous catheter, extending from outside the body to an internal target region of the body, such as an organ, a cavity, and the like. The connectable catheter system, device and method disclosed herein provide a cost effective, safe, robust and efficient catheter system allowing the prolonged use of an indwelling stent placed within a subject's body (for example, in a target organ or cavity).

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As used herein, the term "catheter" is directed to a tube having a continuous, internal lumen and two opposing ends/sections. The two ends may include an external end (located externally to a body of a subject) and an internal end (capable of being located within a body of the subject, for example, in an organ or within a cavity). In some instances, the catheter is configured to allow the transfer of various materials (for example, fluids (including gaseous fluids or liquids)) between (to and from) an external region and an internal region. For example, the catheter may be used to transfer liquids (such as urine) from the bladder (internal organ) to an external location (such as external collecting bag). In some embodiments, the catheter may be rigid, semi-rigid or flexible and may be made of various materials. In some embodiments, the catheter may have various dimensions (length, width, external diameter, internal diameter, and the like). In some embodiments of the present invention, the catheter may be comprised of at least two parts/portions that may connect within the body of the subject to form a continuous catheter tube extending from outside the body of the subject, to an internal location (such as an organ or a cavity). Exemplary internal organs or cavities into which a catheter may be inserted include such organs as, but not limited to: urinary tract (renal pelvis, bladder), heart, intestinal system, uterus, lungs, pleura, gastrointestinal tract, nasal sinus, esophagus, rectum, vagina, stomach, abdomen, peritoneum, liver, kidney and brain, and the like.

As use herein, the terms "main catheter", "connecting catheter" and "intermediary catheter" may interchangeably be used.

As used herein, the term "indwelling" is directed to an article (a device) which is inserted to and located within a subject body for an extended period of time (for example, between several hours and until 12 month; between 12 hours to 8 months, between 1 day to 6 months, between 1 week to 4 months, between 2 weeks to 3 months, between 4 weeks to 2 months). As used herein, the terms "indwelling device'" "indwelling stent", "indwelling catheter" "reconnectable indwelling catheter", "reconnectable indwelling stent", and "reconnectable indwelling device" may interchangeably be used.

As used herein, the term "proximal" is directed to a location which is external to a subject's body. As used herein, the term "distal" is directed to a location which is internal to a subject body.

As used herein, the terms "target organ", "target cavity", "internal target organ", "internal target cavity" may interchangeably be used and are directed to an internal organ/cavity into which or from which materials may be transferred from/to an external location. In some embodiments, the target section of the indwelling stent is located within the target organ.

As used herein, the terms "cavity" and "body lumen" may interchangeably be used. The terms are directed to a closed compartment/structure/organ, within a subject body. Exemplary cavities may include such cavities as, but not limited to: stomas, bladder, kidney, heart, intestines, uterus, lungs, urinary tract, and the like.

According to some embodiments, the present invention provides a connectable catheter system, the catheter system includes a first, (at least partially external) intermediary (main) catheter and a second, internal, indwelling stent, whereby the intermediary catheter and the indwelling stent may be connected, internally, within a subject body to form a continuous conduit (passage), capable of transferring materials (such as fluids) to and from an external location (where one end of the intermediary catheter is located) to an internal body location (such as an organ or cavity), where the indwelling stent is located.

According to some embodiments, the indwelling stent is configured to be inserted into an internal body location (such as an organ/cavity). In some embodiments, the indwelling stent is configured to be retained in the body, for an extended period of time, so as to allow and enable the performance of a number of uses, without the need to repeatedly remove it from the body. According to some embodiments, the target section of the indwelling stent may be fitted with a reversible fixing element that may assist in retaining the indwelling stent in the target area/cavity. For example, when used in the urinary tract, the target section of an indwelling urinary stent may be kept in the renal pelvis by a looped end such that the fixing element may be a string that locks the looped end or a nitinol made member that can ruggedize the looped end to thereby fix the indwelling stent.

Reference is now made to FIG. 1A, which is a schematic illustration of a catheter system, according to some embodiments. As shown in FIG. 1A, the connectable catheter system (1) is comprised of at least two connectable parts/portions: an indwelling stent part (2) and an intermediary catheter part (4). The indwelling stent (2), shown in cross-section in FIG. 1A, is illustrated in the form of a tube (optionally flexible), having an internal lumen (3). Indwelling stent (2) has two opposing ends/sections: a "connecting section" (12) and a "target section" (10), such that target section (1) is closer to (or within) an internal target organ/cavity. In some embodiments, connecting section (12) of indwelling stent (2) may be positioned in or adjacent to an internal body location, and target section (10) may be positioned inside or in close proximity to the target organ/cavity (for example, but not limited to, the renal pelvis).

As further shown in FIG. 1A, intermediary (main) catheter (4) (cross-section depiction) includes two opposing sections (ends): an external (proximal) section (11), and a tip (distal/internal) section (8). As further detailed below, external section (11) includes opening(s) and/or connector(s) that are required for the catheter operation. Tip section (8) is configured to be inserted to a body of a subject.

As further shown in FIG. 1A, intermediary catheter (4) includes, in an internal longitudinal lumen thereof, a stylet (15), between proximal and tip sections (11 and 8, respectively) insertable through opening (18). A tip section (20) of stylet (15), when fully inserted through the internal longitudinal lumen of intermediary catheter (4) protrudes from tip section (8) of intermediary catheter (4). Tip section (20) of stylet (15) is configured to connect to connecting section (12) of indwelling stent (2) and pull it into the inner lumen of intermediary catheter (4). Thereby, when stylet (15) is pulled out from intermediary catheter (4), a continuous fluid conduit is formed between internal lumen (3) of indwelling stent (2) and the internal lumen of intermediary catheter (4). Barrier (5), located in the internal longitudinal lumen of intermediary catheter (4), is configured to limit the retraction of stylet (15), when connected to indwelling stent (2). Intermediary catheter (4) further includes an inflation conduit (not shown), extending from inflation port (24) to an inflatable anchoring balloon (14) located at an external surface of tip section (8) of intermediary catheter (4). Inflation of inflatable anchoring balloon (14) may be achieved by connecting a source of fluid (such as, gas (for example, air), or liquid (such as, water, sterile saline)), to inflation port (24) located at the external section of intermediary catheter (4), wherein the inflation may be conducted utilizing a valve, such as a check valve. Inflatable anchoring balloon (14) is represented in an inflated configuration by a dashed line and in a deflated configuration by a solid line. Intermediary catheter (4) further includes, at an inner lumen thereof, a securing member (27). Securing member (27) is configured to secure connecting section (12) of indwelling stent (2) within the inner lumen of an intermediary catheter (4), in tip section (8) thereof. Securing member (27) is represented in an inflated configuration by a dashed line and in a deflated configuration by a solid line. Intermediary catheter (4) further includes an additional inflation conduit (not shown), extending from inflation port (25) to securing member (27). Securing member (27) may further be configured to seal fluid passage outside of indwelling stent (2). In some embodiments, as further detailed below, the intermediary catheter includes a separate sealing member in addition to the securing member.

Figure 1B:
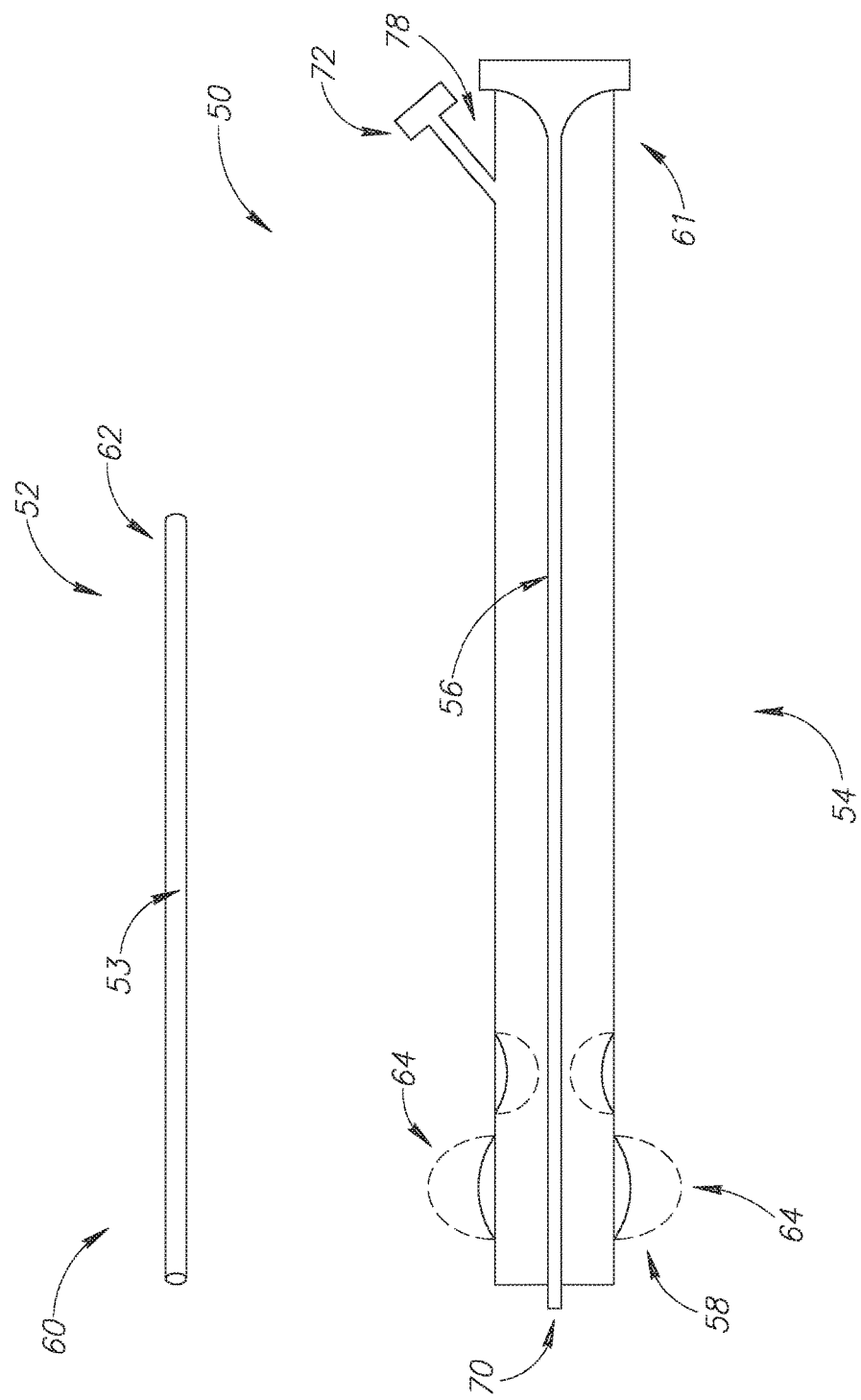

Reference is now made to FIG. 1B, which is a schematic illustration of a catheter system, according to some embodiments. As shown in FIG. 1B, the connectable catheter system (50) is comprised of at least two connectable parts/portions: an indwelling stent part (52) and an intermediary catheter part (54). The indwelling stent (52), shown in cross-section in FIG. 1B, is illustrated in the form of a tube (optionally flexible), having an internal lumen (53). Indwelling stent (52) has two opposing ends/sections: a "connecting section" (62) and a "target section" (60). In some embodiments, connecting section (62) of indwelling stent (52) may be positioned in or adjacent to an internal body location, and target section (60) may be positioned inside or in close proximity to the target organ/cavity (for example, but not limited to, the renal pelvis).

As further shown in FIG. 1B, intermediary (main) catheter (54) (cross-section depiction) includes two opposing sections (ends): an external (proximal) section (61), and a tip (distal/internal) section (58). As further detailed below, external section (61) includes opening(s) and/or connector(s) that are required for the catheter operation. Tip section (58) is configured to be inserted to a body of a subject.

As further shown in FIG. 1B, intermediary catheter (54) includes, in an internal longitudinal lumen thereof, an internal catheter (56), insertable between proximal and tip sections (61 and 58, respectively) through opening (78). A tip section (70) of internal catheter (56), when fully inserted through the internal longitudinal lumen of intermediary catheter (54) protrudes from tip section (58) of intermediary catheter (54). Tip section (70) of internal catheter (56) is configured to connect to connecting section (62) of indwelling stent (52) and form a continuous fluid conduit. Intermediary catheter (54) further includes an inflation conduit (not shown), extending from inflation port (72) to an inflatable anchoring balloon (64) located at an external surface of tip section (58) of intermediary catheter (54). Inflation of inflatable anchoring balloon (64) may be achieved by connecting a source of fluid (such as, gas (for example, air), or liquid (such as, water, sterile saline)), to inflation port (72) located at the external section of intermediary catheter (54), wherein the inflation may be conducted utilizing a valve, such as a check valve. Inflatable anchoring balloon (64) is represented in an inflated configuration by a dashed line and in a deflated configuration by a solid line.

Figure 2:
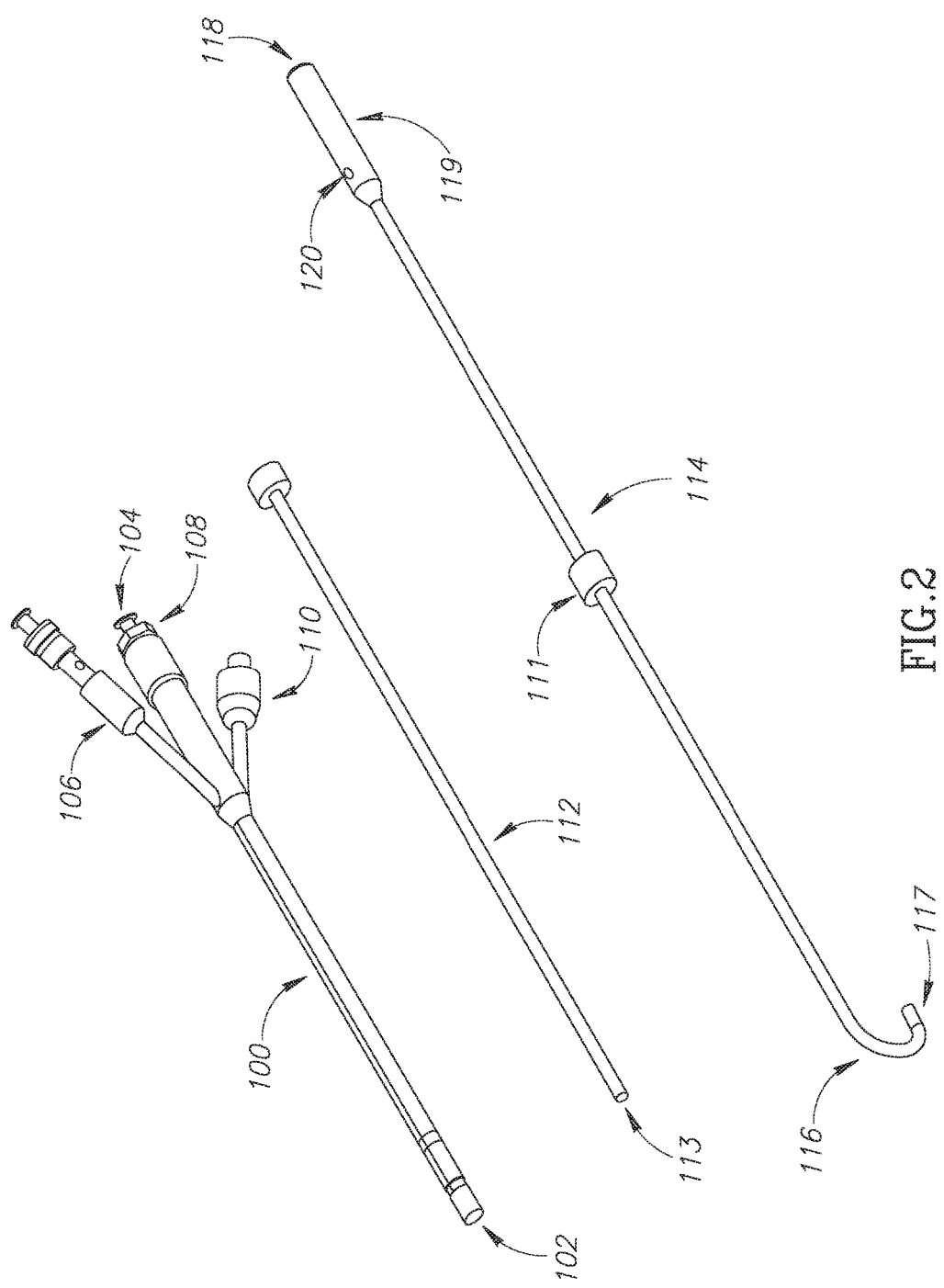
FIG. 2—a schematic perspective view of an intermediary catheter, according to some embodiments.
Figure 3A:
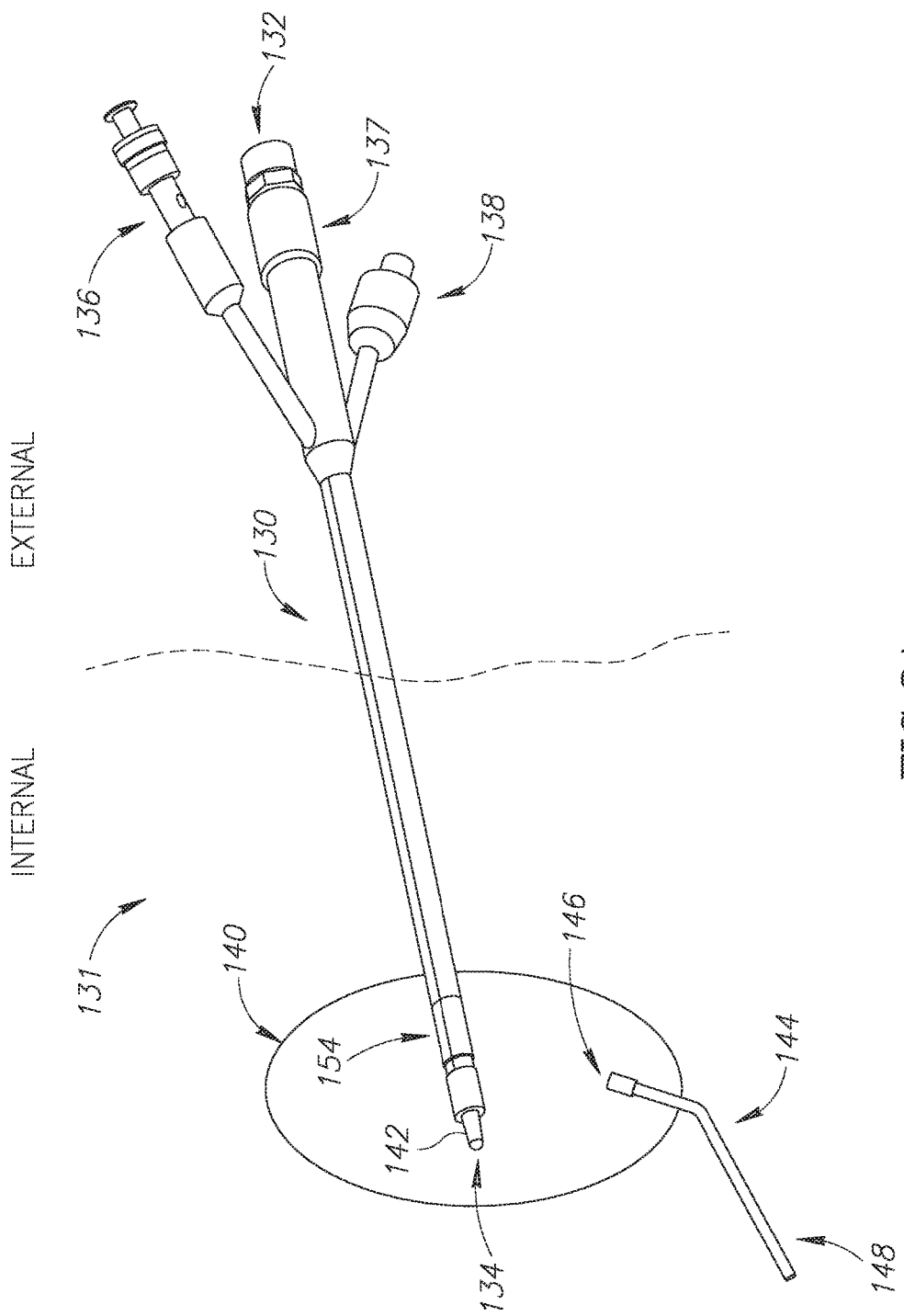
FIGS. 3A-B—schematic perspective illustrations of a connectable catheter system located within an internal body region, according to some embodiments.
Figure 3B:
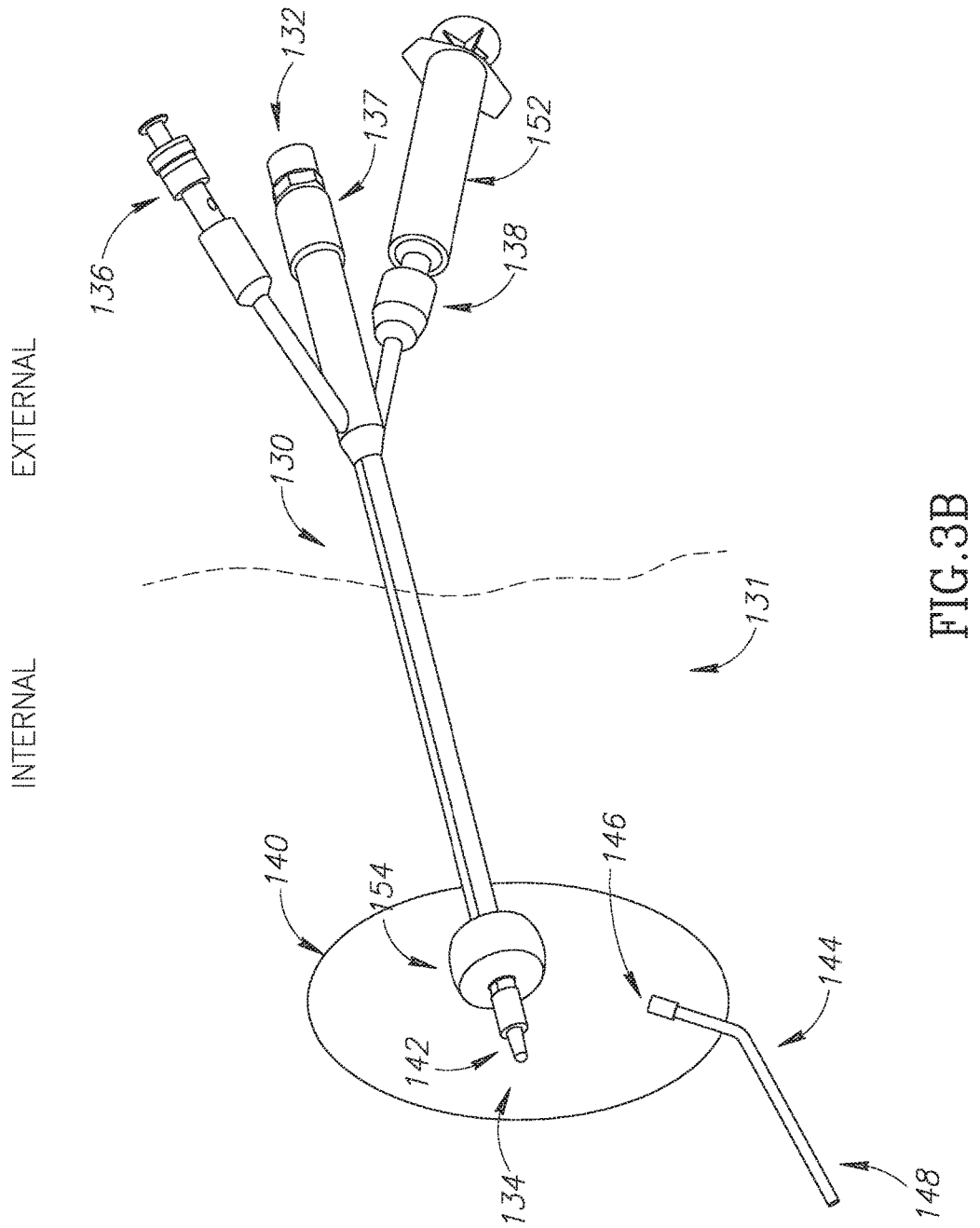

Reference is now made to FIG. 2, which is a schematic illustration of an intermediary (main) catheter, according to some embodiments. As shown in FIG. 2, intermediary catheter (100) has an external (proximal) section (104) and a tip (distal/internal) section (102). Intermediary catheter (100) has one or more openings or connectors or ports at the external section thereof, each configured to be connected to one or more devices and/or transfer different materials, via one or more inner lumens, that may be parallel to each other and may be identical, similar or different in length, composition or diameter. The exemplary intermediary catheter (100) illustrated in FIG. 2, includes three connectors (shown as connectors 106, 108 and 110). For example, connector 106 may be used to connect to a fluid transferring device (such as a syringe), for transferring fluids (for example, via an internal lumen located within the walls of the intermediary catheter), that can, for example, inflate/deflate an internal securing element, such as a securing balloon, or a sealing member, located on the inner walls of the intermediary catheter, the balloon is configured to secure the indwelling stent within the intermediary catheter, as further detailed below. For example, connector 110 may be used to connect to a fluid transferring device (such as syringe), for transferring fluids that can, for example, inflate/deflate an anchoring balloon, located on (or associated with) the outer walls of intermediary catheter (100), configured to secure the intermediary catheter in an internal body location (such as a body organ or cavity), as further detailed below. For example, connector 108 may be used to connect to a fluid transferring device (such as syringe), for transferring fluids from external section (104) of intermediary catheter (100) into the subject body. For example, connector (108) may be used to connect/guide various articles/devices that may be used in the placement and/or operation of the intermediary catheter. For example, guide rod (112) may be inserted via connector (108), through an inner lumen of intermediary catheter (100), such that that tip (113) thereof may protrude through tip section (102) of intermediary catheter (100) and may be used for guiding the insertion of the intermediary catheter into the subject body. In some embodiments, the guide rod may be a guide wire or mandrel. In some embodiments, as further detailed below, guide rod (112) may further be used for removing/disconnecting/pushing the indwelling stent from the intermediary catheter. For example, a stylet (shown as stylet 114) may be inserted via connector 108, through the inner lumen of intermediary catheter (100) such that it may protrude through the tip section (102) thereof and may be used for catching, connecting and/or maneuvering the indwelling stent. As shown in FIG. 2, exemplary stylet (114) has a tip section (tip 116) which includes at the tip a connecting member (117), that may specifically interact and connect with an internal indwelling stent. The external section of stylet (118) may include a handle (119) that may be used for controlling and maneuvering stylet (118). Stylet (114) may further include a connector (111) allowing the connection and/or securing of the stylet to intermediary catheter (100). The external section of stylet (118) may further include or associate with various indicators, such as a connection indicator (120) which is configured to provide an indication, such as: that a connection between the intermediary catheter (for example, via the stylet) and the indwelling stent has been achieved (as further detailed below); an indication that a continuous fluid passage (conduit) is formed between the inner lumens of the intermediary catheter and the indwelling catheter, and the like. The intermediary catheter may further include a securing member located at an inner lumen of the tip section thereof, wherein the securing member is configured to secure a connecting section of an indwelling stent within the inner lumen of the tip section of the intermediary catheter, to allow formation of a continuous fluid conduit between the inner lumen of the connectable catheter and an inner lumen of the indwelling stent. The securing member may further be used as a sealing member, configured to seal the continuous fluid conduit between the inner lumen of the connectable catheter and an inner lumen of the indwelling stent. In some embodiments, a separate sealing member is used to seal the continuous fluid conduit between the inner lumen of the connectable catheter and an inner lumen of the indwelling stent. In some embodiments, the sealing member can prevent or overcome decoupling forces that may be exerted when the fluid provided is viscous Reference is now made to FIGS. 3A-B, which are schematic perspective illustrations of components of a connectable catheter system (131) located within an internal body region, according to some exemplary embodiments. As shown in FIG. 3A, intermediary catheter (130) includes three connectors (136, 137 and 138) at the external section (132) thereof, which is located outside the body ("External"). The tip section (134) of intermediary catheter (130) is located within the body ("Internal"), for example, within a body cavity (140). The dashed line (131) is an imaginary line, separating between external body region ("External") and internal body region ('Internal"). In the exemplary system shown in FIG. 3A, protruding through the inner lumen and from the tip section (134) of intermediary catheter (130), a distal tip (142) of a guide rod is shown. Anchoring mechanism (154), shown in the form of a deflated balloon, is located on an external surface of intermediary catheter (130). Further shown in FIG. 3A is indwelling stent (144), having its connecting section (146) located within body cavity (140) and the target section (148) located, for example, within a target organ/cavity. As shown in FIG. 3B, a syringe (152) is connected to connector (138), wherein the syringe is used to activate the anchoring mechanism by inflating balloon (154). The anchoring mechanism/element (such as anchoring balloon 154) is used to lock/fix the intermediary catheter in its internal location within the subject body (such as, within a body cavity).

Figure 4A:
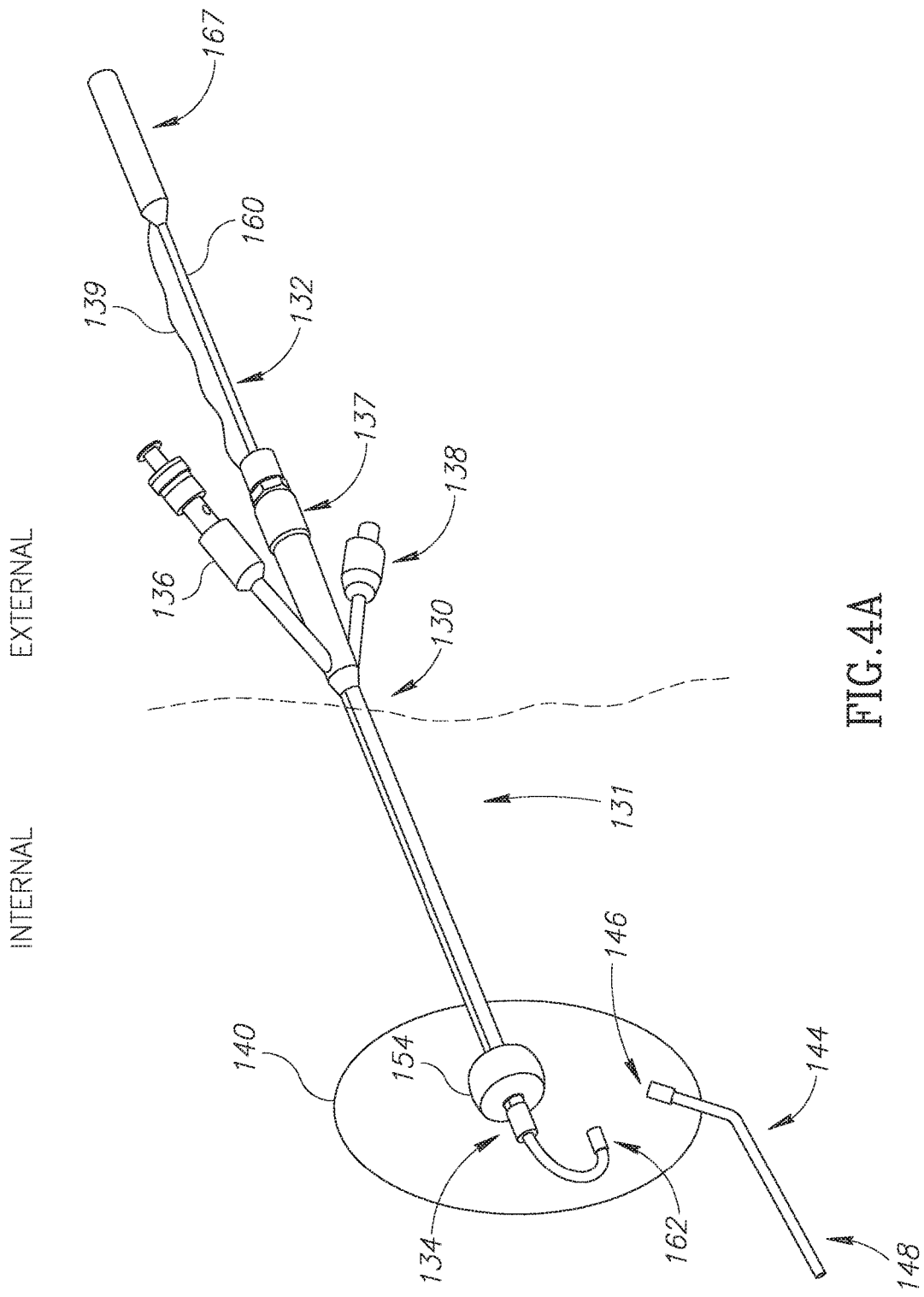
FIGS. 4A-C—schematic perspective illustrations of an exemplary connection establishment, within a subject body between the intermediary catheter and the indwelling stent, according to some embodiments.
Figure 4B:
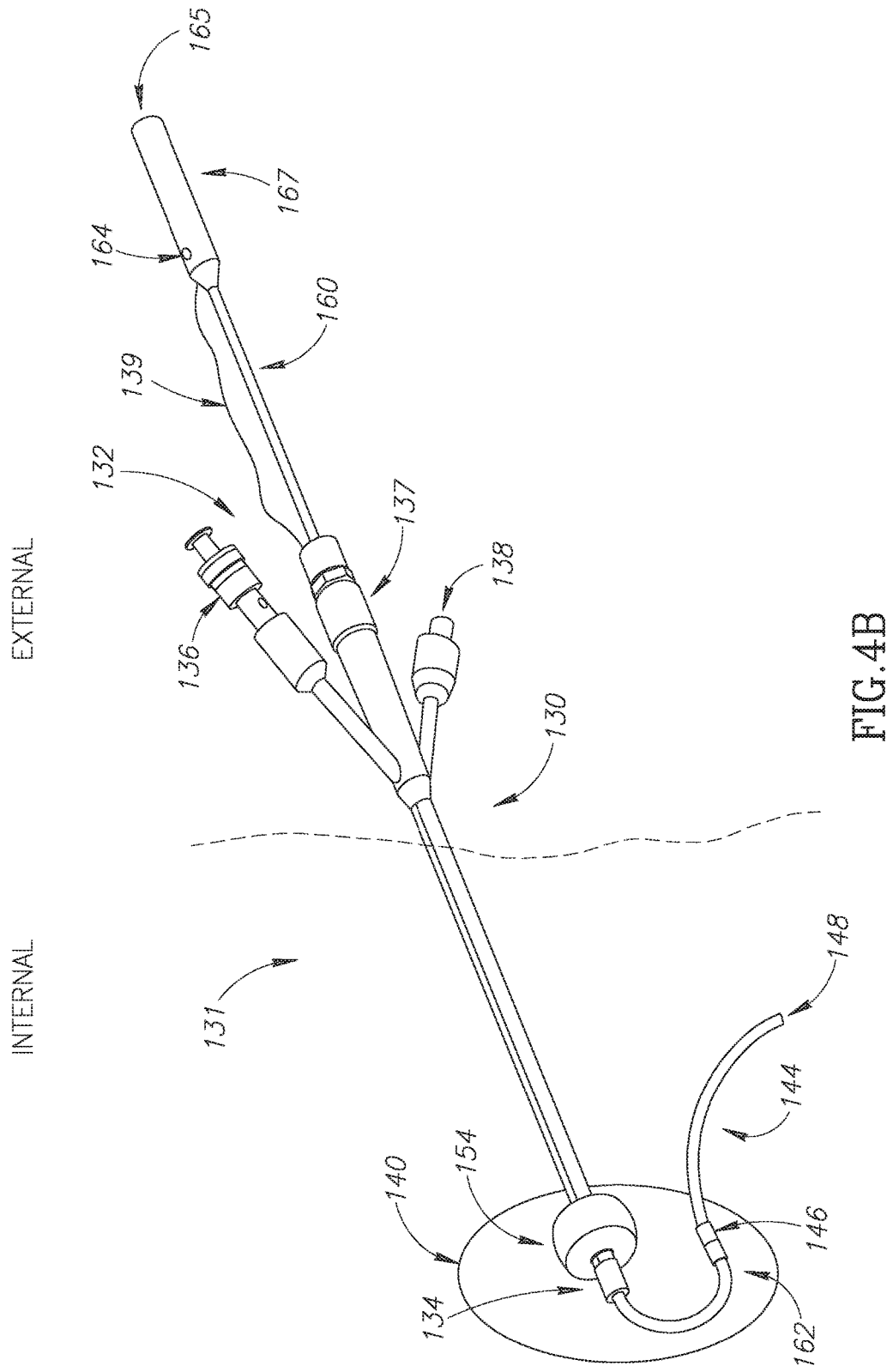
Figure 4C:
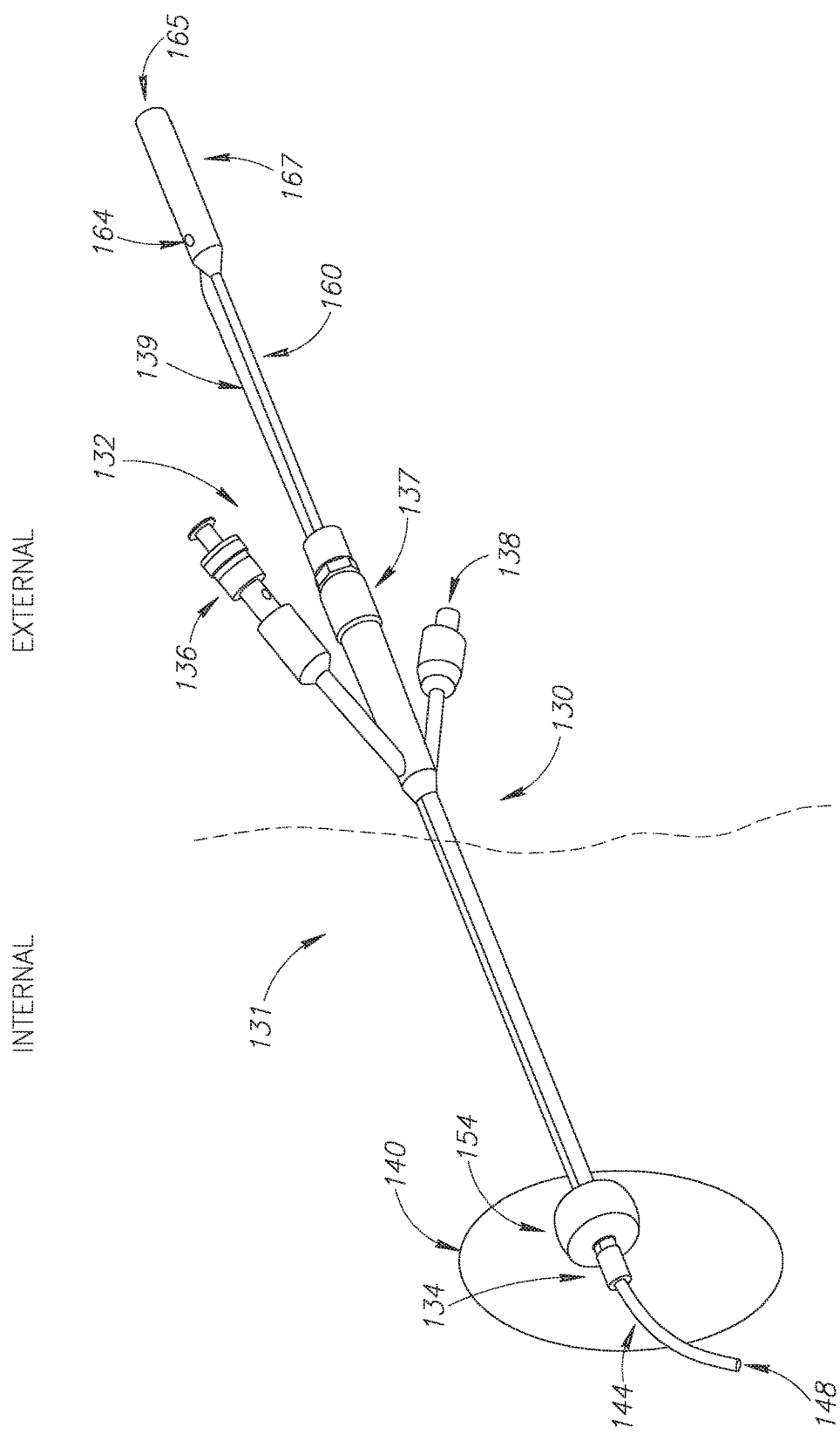

Reference is now made to FIGS. 4A-C, which are schematic perspective illustrations of exemplary connection establishment, within a subject body between the intermediary catheter and the indwelling stent, according to some embodiments. As shown in FIG. 4A, to exemplary system (131) presented in FIGS. 3A-B, an exemplary stylet (160), may be removably inserted from external section (132) of intermediary catheter (130), for example, via, connector (137), through the inner lumen of intermediary catheter (130) and protruding through tip section (134) of intermediary catheter (130). The tip section (162) of stylet (160) may be associated with or integrally formed with an attachment member configured to attach/connect to connecting section (146) of indwelling stent (144). Handle (167) of stylet (160) may be used to operate and/or maneuver the stylet. Further shown is string (139), in a relaxed position. As shown in FIG. 4B, tip section (162) of stylet (160) is connected to connecting section (146) of indwelling stent (144). The connection between the tip section of the stylet and the connecting section of the indwelling stent may be achieved by various mechanisms/attachment members, as further detailed below. Exemplary connecting/attachment members include such mechanisms as, but not limited to: magnets, vacuum, "pig-tail" structure, lasso structure, a loop structure, a net, a basket structure or any combination thereof. In some embodiments, the stylet may further include or be functionally associated with an indication unit configured to provide an indication of a connection between the attachment member of the stylet and the connecting section of the indwelling stent. An exemplary indication unit (164), located at handle (167) in the external section (165) of stylet (160) is illustrated in FIG. 4B. Further shown is string (139), connected between external end (132) of intermediary catheter (130) and external end (165) of stylet (160). String (139) may be in a relaxed position (as shown in FIG. 4B) or in a stretched position (FIG. 4C, below), depending on the location of stylet (160) within intermediary catheter (130). String (139) may be used for the maneuvering of the stylet and/or to control/limit the extent that the stylet can be pulled out of the intermediary catheter, once the stylet is connected to the indwelling catheter, to thereby serve as a securing/stopper member. Once connected to the indwelling stent (144), stylet (160) may be operated by a user (for example, by using handle (167)), to maneuver the indwelling stent and to place the connecting section thereof inside the tip section lumen region (134) of intermediary catheter (130), so as to form a secure, continuous fluid passage/conduit between intermediary catheter (130) and indwelling stent (144). Thus, when stylet (160) is proximally retracted (towards the external end) within the inner lumen of intermediary catheter (132), the connecting end of indwelling stent (144) is pulled into the inner lumen of the intermediary catheter. As shown in FIG. 4C, when stylet (160) is proximally retracted within the inner lumen of intermediary catheter (132), string (139) acquires a stretched position, which limits the further pulling of stylet (160) out of the intermediary catheter. By this mode, the string serves as a securing/stopper member which secures the connection between the indwelling stent and the stylet, within the inner lumen of the intermediary catheter.

Figure 5A:
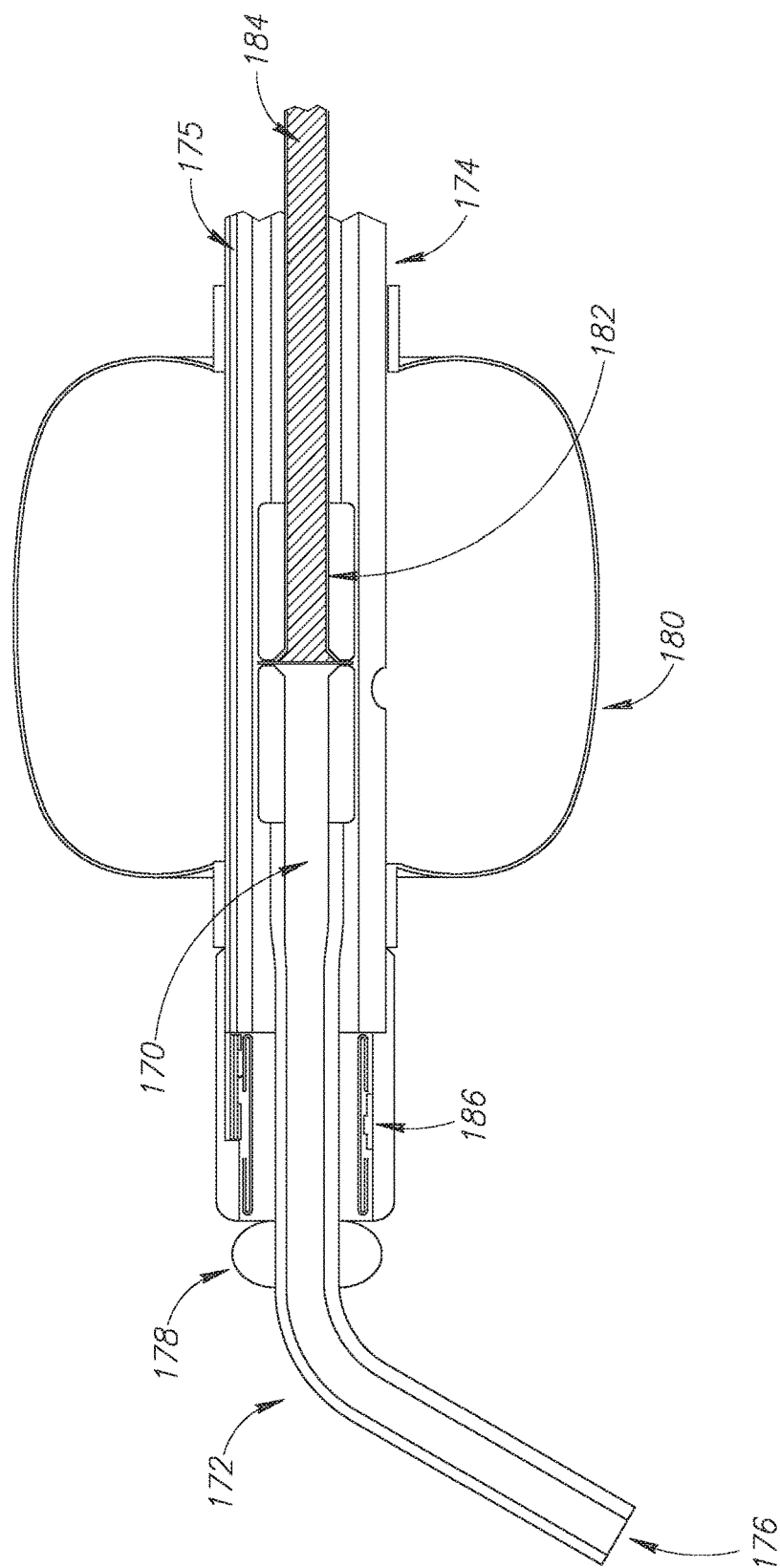
FIGS. 5A-D—schematic close-up views of a cross section of the tip section of an intermediary catheter being connected to an indwelling stent, according to some embodiments.

Reference is now made to FIGS. 5A-D which show close-up views of a cross section of the tip section of an intermediary catheter being connected to an indwelling stent, according to some embodiments. As shown in FIG. 5A, connecting section (170) of indwelling stent (172) is located within the inner tip section lumen of intermediary catheter (174), while the target section (176) of the indwelling stent (172) is not inserted into inner lumen of intermediary catheter. As further shown in FIG. 5A, indwelling stent (172) includes a stopper element (shown as stopper element 178). The stopper element may be located at the outer wall of the indwelling stent at a location between the connecting section and the target section. In some embodiments, the stopper element is configured to determine the portion (length) of the indwelling stent that can enter the inner lumen of the intermediary catheter, thus locating the securing member and sealing member on the intermediary catheter in an accurate position relative to the indwelling stent for best functionality. In some embodiments, the indwelling stent may have one or more regions having special shape(s), such as an increased diameter that may increase the holding power of an inflated inner balloon and increase securing and sealing of the connection. In some embodiments, the stopper element may reside on the entire circumference of the indwelling stent or on portions thereof. In some embodiments, the stopper element is a stopper ring. Further shown in FIG. 5A is an anchoring element (shown as anchoring balloon 180) configured to anchor intermediary catheter (174) to its location within the subject's body. Further shown are the connecting section (170) of the indwelling stent (172) connected to connecting member (182) of stylet (184) that has been inserted via the internal lumen of the intermediary catheter (174), as detailed above. Additionally, on the inner walls of the tip section of the intermediary catheter, a securing member (186) is located. The securing member may be configured to secure the connecting section of the indwelling stent within the inner lumen of the tip section of the intermediary catheter. The securing member may be deployable and may include one or more inflatable balloons that may be inflated, for example, via an inflation lumen (175), which may be located adjacent to the internal lumen of the intermediate catheter (for example, in the inner walls of the intermediate catheter), using, for example, a syringe connected to a connector located on the external section of the intermediary catheter. In some embodiments, the securing member may include any one of securing means, such as, but not limited to: a securing balloon, an internal stopper ring, one or more recesses on the inner walls of the tip section of the intermediary catheter and/or on the outer walls of the connecting section of the indwelling stent, vacuum means, magnets, an internal or external locking mechanism such as a rod inserted through the intermediary catheter that can be rotated to engage a recess on the magnet or other part of the indwelling stent, and the like, or combinations thereof. In some embodiments, the securing member is further used to seal the connection between the indwelling catheter and the intermediary catheter so as to form a continuous fluid conduit. In some embodiments, the system may further include a sealing element/member that may be used to seal the connection between the indwelling catheter and the intermediate catheter, so as to form a continuous (leakage free) fluid passage (conduit). In some embodiments, the sealing member is in addition to the securing member. In some embodiments, the sealing member is instead of the securing member. In some embodiments, the system further includes means/controllers for identifying and verifying the connection between the intermediary catheter and the indwelling stent and/or verification of the formation of a continuous catheter having a continuous fluid passage there within. In some embodiments, the verifications means may include such means as, but not limited to: electric impedance sensor, internal air pressure sensor, magnetic proximity sensor, fluid pressure sensor, and the like, or any combination thereof.

Figure 5B:
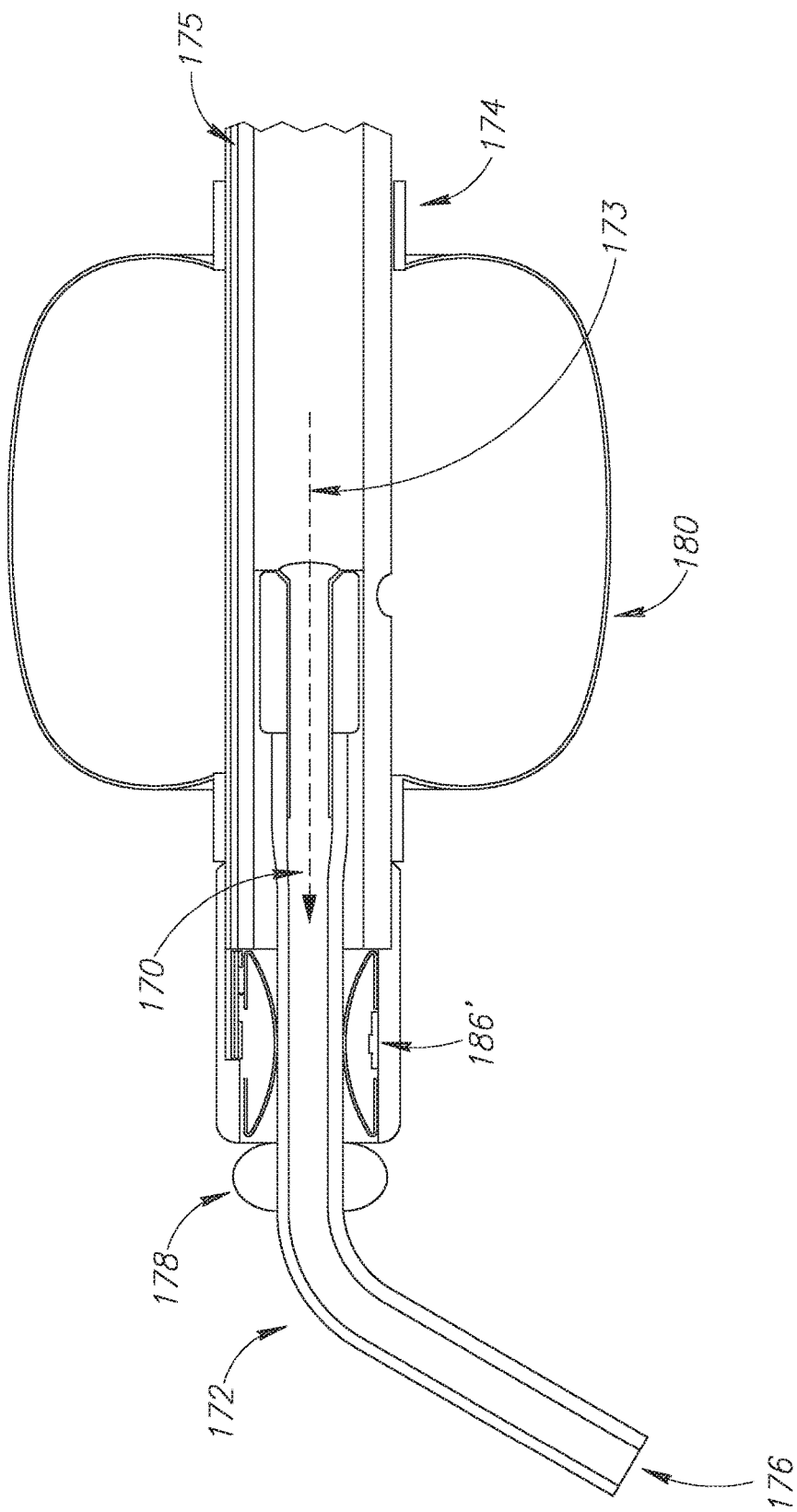

Reference is now made to FIG. 5B, which shows the formation of a continuous catheter enabling a continuous passage of fluids and other materials, according to some embodiments. As shown in FIG. 5B, securing member (186') has obtained an inflated position, while securing the connecting section of the indwelling stent (170) into its location within the inner lumen of the intermediary catheter. As further shown in FIG. 5B, the stylet has been removed, and a continuous fluid passage (conduit) is formed, allowing transfer of materials from/to the proximal (external) end of the intermediary catheter, via the tip section thereof, the connecting section of the indwelling stent and to/from the target section of the indwelling stent. The exemplary fluid flow is represented by dashed lines (173). The materials transferred through the continuous catheter may be applied/removed/injected via a connector on the external section of the intermediary catheter. After the desired materials have been transferred to the designated locations, the indwelling stent may be disconnected from the intermediary catheter. The disconnection of the indwelling stent from the intermediary catheter may be performed by various means. For example, a guide rod (such as mandrel or guide wire) may be inserted thought the external section of the intermediary catheter, via the internal lumen of the intermediary catheter, to push the indwelling stent out from the intermediary catheter. The disconnection of the indwelling stent may be performed after disengaging the securing member which secures the connecting section of the end of the indwelling stent within the tip section region of inner lumen of the intermediary catheter. In some embodiments, the disconnection may be achieved by use of external magnets, capable of separating the connecting section of the indwelling stent from the tip section of the intermediary catheter.

Figure 5C:
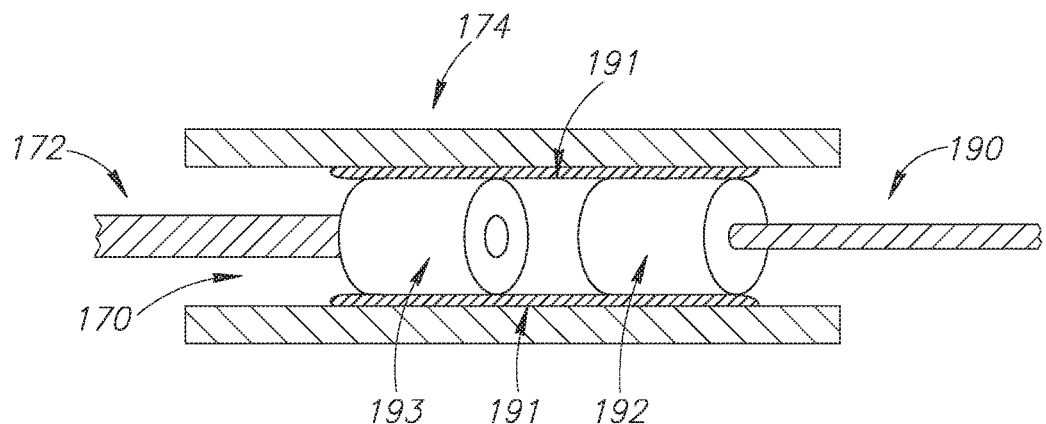
Figure 5D:
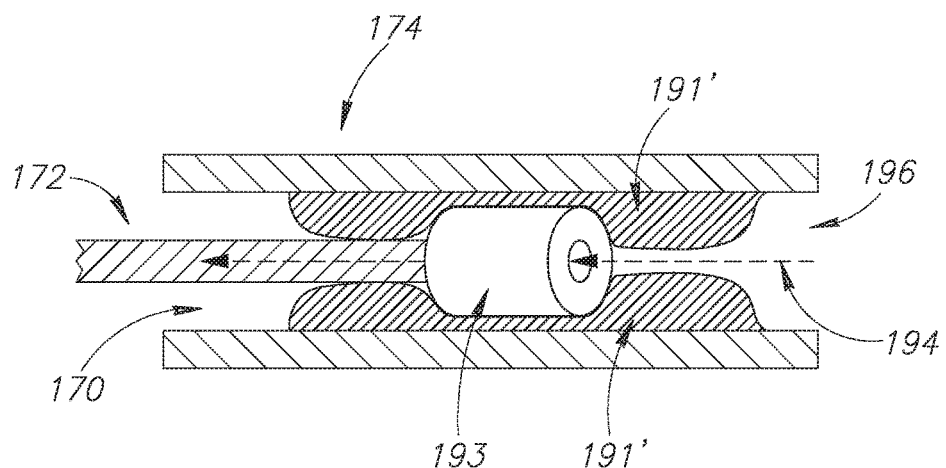

As shown in FIG. 5C, which is a close up view of a cross section of the tip section region of intermediate catheter (174), the connecting section (170) of indwelling stent (172) is located within the inner tip section lumen of intermediary catheter (174). The connecting section includes an attachment member (193), shown in the form of a hollow magnet, which is connected to a corresponding attachment member (192) located at the tip section of stylet (190). Further shown is deployable securing member (191). Securing member (191) may serve as a deployable securing member that is configured to secure the connecting end (170) of indwelling stent (172) within the inner lumen of intermediary catheter (174) and/or to further provide a sealing of the connection between the indwelling stent and the intermediate catheter lumens. As shown in FIG. 5D, the stylet has been removed from inner lumen (196) of intermediate catheter (174), and securing member (191') has acquired an inflated formation, thereby sealing the connection between indwelling catheter (172) and intermediate catheter (174) and forming a continuous fluid passage (conduit), represented by dashed arrow (194).

As detailed above, the approximation/connection/attachment between the connecting section of the indwelling stent and the tip section of the intermediary catheter may be achieved by various means. For example, magnets with opposing polarities may be mounted on the connecting section of the indwelling stent and on the tip section of the intermediary catheter, such that when the two ends are in close proximity, they may magnetically attract and connect. For example, structures configured to attach to each other may reside on the respective ends of the indwelling stent and the intermediary catheter. Such structures may include such structures as, but not limited to: lasso, "pig-tail", net, basket structure, and the like. For example, vacuum ducts located on the tip section of the intermediary catheter may be used to attract the connecting section of the indwelling stent.

According to some embodiments, the system may further include a verification member, configured to verify that the components of the system can specifically interact and connect and form a secure, continuous catheter. In some embodiments, the verification member allows the formation and/or operation of the continuous catheter system. In some embodiments, the connecting section of the indwelling catheter and/or the tip section of the intermediate catheter and/or the tip section of the stylet (or the attachment member thereof) include a verification member. In some embodiments, the verification member is an RFID element, configured to identify a corresponding member on a corresponding interacting part. The use of such verification member provides an added safety means to ensure that the system parts are compatible and can indeed securely and safely connect within the subject body.

Figure 6C:
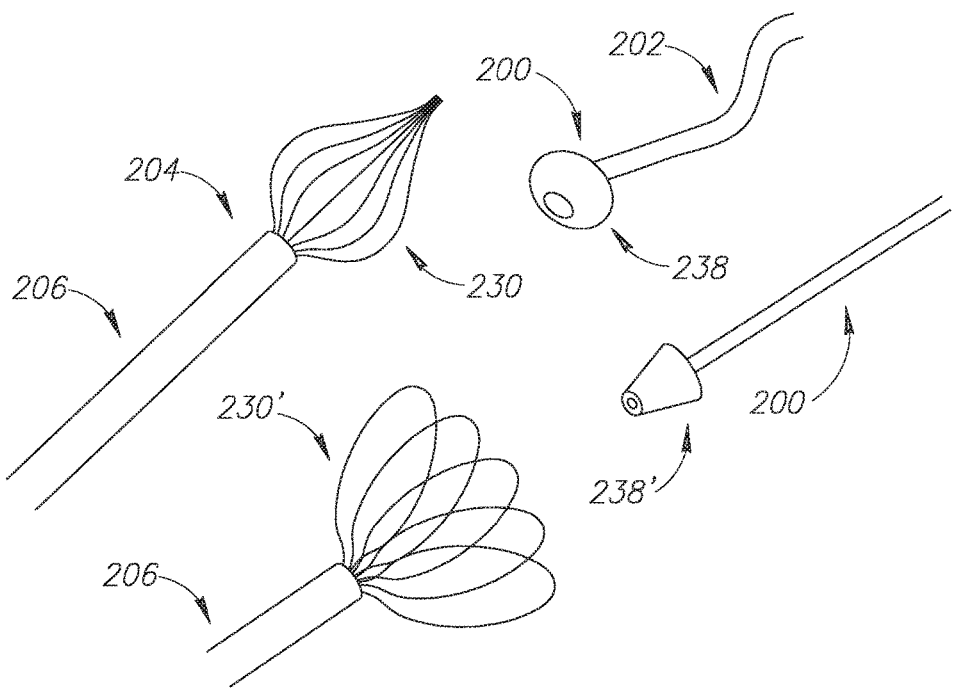

Reference is now made to FIGS. 6A-D, which show schematic illustrations of exemplary means for approximating and/or connecting and/or securing the connection of the tip section of an intermediary catheter with the connecting section of the indwelling stent, according to some embodiments. FIG. 6A, shows a cross section of the connecting section (200) of the indwelling stent (202) and the tip section (204) of the intermediary catheter (206), which include or are attached to magnets of opposite polarities (exemplary shown as hollow cylindrical magnetic tips, (212A-G) on tip section (204) of intermediary catheter (206) and magnetic tips (214A-G) on connecting section (200) of indwelling stent (202). Further shown are internal lumen (208) of indwelling catheter (202) and internal lumen (210) of intermediary catheter (206). FIG. 6B shows a front view of the respective sections presented in FIG. 6A. When the magnetic tips (212A-G) of tip section (204) of intermediary catheter (206), is in proximity to the corresponding magnetic tips (214A-G) of the connecting section (200) of indwelling stent (202), the magnetic attraction causes the tips to attach to one another, thus creating a continuous conduit (shaft/passage/channel) through the lumens (208, 210) of the respective indwelling stent (202) and the intermediary catheter (206) and the hollow magnets connecting them. Alternatively, magnetic particles may be present on one of the tip section of the intermediary catheter or the connecting section of the indwelling stent and magnetizable particles may be present on the other component. In some embodiments, means may be provided to ensure an end to end attachment of the two catheters and prevent a side by side attachment. For example, an inflatable balloon (not shown) may be present around the tip section of the intermediary catheter lumen (210) which prevents the connecting section of the indwelling stent from forming a side by side attachment to the lumen 210.

As shown in FIG. 6C, a three-dimensional basket structure that may have an open/closed position may be used for approximating and attaching the respective ends of the indwelling and the intermediary catheter. As shown in the top panel of FIG. 6C, the basket (230) is in a closed position, and is attached or is integral to the tip section (204) of the intermediary catheter (206). The connecting section (200) of the indwelling stent (202) has a corresponding structure (238), configured to attach or be inserted into the basket. As shown in the bottom panel of FIG. 6C, the basket (230') is shown in an open position (for example, after being inserted into the body and placed in the corresponding cavity/lumen). The open basket (230') may then close over the indwelling stent connecting section, that is structured or attached to a structure (238'), which can provide an adequate anchor for the basket.

Figure 6D:
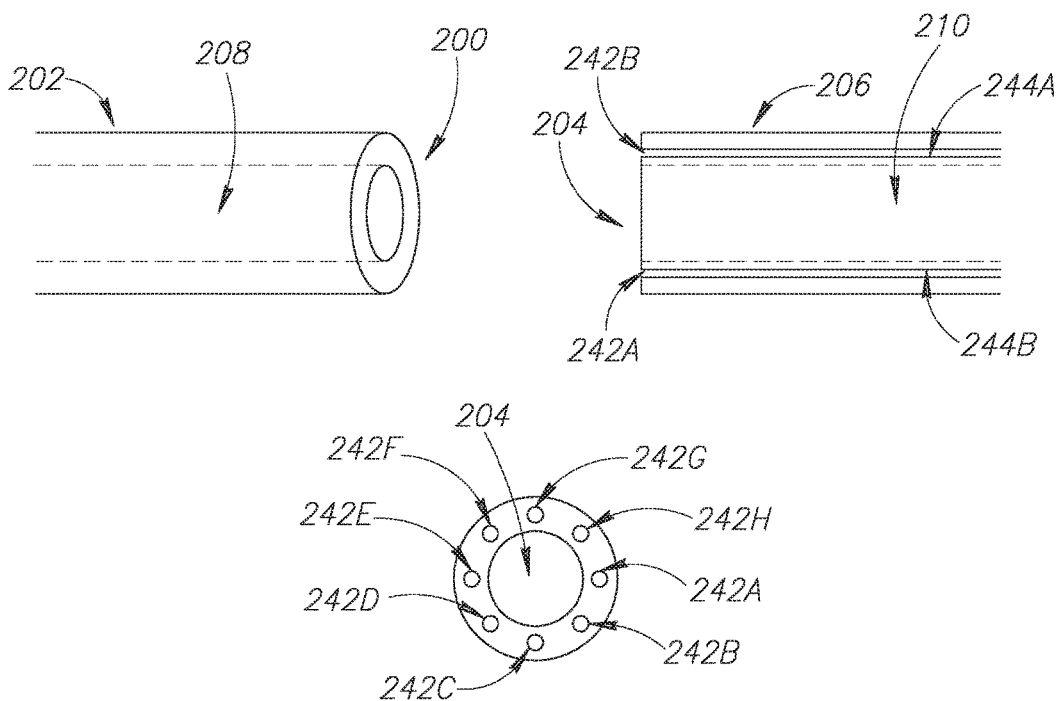

According to some embodiments, after the respective ends of the intermediary catheter and the indwelling stents are attached, the indwelling stent may be pulled into the internal distal (tip section) lumen (shaft) of the intermediary catheter. For example, if magnets were used to attach the respective ends, both magnets would enter that shaft. In the case that the magnets are attached side-by-side, entering the shaft will either force them to realign to face-to-face attachment or they will get detached and the process of attraction and attachment can be retried. When the magnets are attached inside the shaft, a securing/locking mechanism may be applied to secure/lock their attachment. In some embodiments (as exemplified above herein), the magnets may be pulled into the shaft toward a specific position and stopped, for example, by use of a stopper element, such as stopper ring (as exemplified in FIG. 5A), or an external string (as exemplified in FIGS. 4B-C). When the magnets are in position, an internal anchoring/securing element (such as internal anchoring balloon) may be inflated to lock the magnets together. Inflation of such balloon may be achieved, for example, by connecting a source of liquid or gaseous fluid (such as a syringe filled with sterile saline), to a connector located on the external section of the intermediary catheter. Alternatively or additionally, a vacuum seal may be formed between the respective ends of the intermediary catheter and indwelling stents. As shown in FIG. 6D, one or more vacuum ducts (shown as exemplary ducts 244A-B) may extend along the wall of an internal lumen (210) of the intermediary catheter (206), that terminate at the external end of the lumen in a connector (not shown) which can be connected to a source of negative pressure. The vacuum ducts may terminate in apertures, (shown as exemplary apertures 242A-H) in tip section (204) of intermediary catheter (206). When the respective ends of the intermediary catheter and indwelling stents are in proximity to each other in the subject's body, the ends are drawn towards each other by the vacuum created in the vacuum ducts to form a stable fluid-tight connection.

According to some embodiments, there is thus provided a connectable catheter system, comprising: an intermediary catheter comprising an external section and a tip section, the tip section is configured to be inserted into a body of a subject; an indwelling stent, configured to be located within the body of the subject, the indwelling stent comprises a connecting section and a target section; wherein the connecting section of the indwelling stent is configured to reversibly connect, within the body of the subject, to the tip section of the intermediary catheter to form a continuous conduit from the external section of the connectable catheter to the target section of the indwelling stent.

According to some embodiments, the indwelling stent may be designed to have articulation and manipulation capabilities that enable increased control over the locale of fluids passage (fluid target location). In some embodiments the articulation is implemented by one or more (such as, two or more) strings that are inserted through the indwelling stent lumen such that pulling any of the strings may change the angle and direction of the target section of the indwelling stent. Combining the change of direction, the target section of the indwelling stent and the controlled pulling or pushing enables relocation of the indwelling stent target section essentially to any desired location in the target cavity. In some embodiments, the articulating strings are connected within the attachment member of the indwelling stent to the intermediary catheter. In some embodiments the articulating strings are passed externally to the indwelling stent, through the body cavity to outside the subject's body.

In some embodiments a ring of radio-opaque pignebt is inserted over the catheter tip section to enable the tracking of the tip location by an external x-ray system.

In some embodiments, the intermediary catheter may be provided with a radio-opaque tip in order to locate the tip in radiographic images.

In some embodiments the tracking of the tip location is enabled by a miniature camera device connected to the catheter tip section. Such cameras, with typical pixel dimension of between 1 to 2.5 micro-meter are available in matrixes that are small enough, for example 100 micrometers length, to be inserted via an indwelling stent.

According to some embodiments, the target section of the indwelling stent may be shaped or formed in one or more loops to anchor it and retain its position within the target cavity. In some embodiments a string may be attached to the anchoring loop in a way that when the string is tightened, it secures the anchoring loop to prevent opening thereof under pull forces, which may result in misplacing the correct positioning within the target body cavity. This string can be a lumen and may be connected to the target section. In some embodiments the string can be one of the strings that are used for the indwelling stent articulation. In some embodiments, the string can have internal tension such that it would acquire an open position when released externally from tightening when inserted through the indwelling stent internal lumen.

In some embodiments, alternative anchoring mechanisms may be used for retaining the position of the indwelling stent in its target location, such as, for example, a Nitinol rod inserted into the target section of the indwelling stent, which may strengthen the loop holding force.

According to some embodiments, the connecting section of the indwelling stent is configured to fit into an inner lumen of the tip section of the intermediary catheter.

In some embodiments, the inner lumen of the intermediary catheter includes a securing member configured to secure the connecting section of the indwelling stent within the inner lumen of the tip section of the intermediary catheter. In some embodiments, the securing member is deployable. In some embodiments, the securing member may include one or more inflatable balloons. According to some embodiments, the intermediary catheter may further include an inflating port/connector configured to inflate the one or more inflatable balloons. In some embodiments, the securing member includes vacuum ducts. In some embodiments, the securing member is mechanical and includes corresponding recesses or grooves in the respective catheter ends. In some embodiments, the mechanical securing member includes matching interacting hooks, capable of securing the catheters ends. In some embodiments, the securing member includes a flexible plate (leaf). In some embodiments, the flexible plate is made of metal. In some embodiments, when an inner securing balloon is used, the flexible metal plate may be fitted on top of the inner securing balloon, such that it may move into the path of the connecting section of the indwelling catheter, when the securing balloon is inflated, thus creating a mechanical lock that secures the connection section of the indwelling stent, within the intermediary catheter tip section (within the inner lumen thereof). In some embodiments, the securing member is configured to reversibly secure the connecting section of the indwelling stent within the inner lumen of the tip section of the intermediary catheter. According to some embodiments, more than one securing member (identical, similar or different) may be configured to act in parallel. According to some embodiments, the securing member may be further configured to seal a fluid passage between the outer wall of the indwelling stent and the inner wall of the indwelling stent, so as to form a continuous conduit, with no leakage of fluid passing therein. In some embodiments the sealing member is a separate member, capable of sealing a fluid passage between the outer wall of the indwelling stent and the inner wall of the indwelling stent, which is placed in addition to or alternatively to the securing member. In some embodiments, the sealing member is deployable.

According to some embodiments, the catheter system may further include a stylet removably insertable into the inner lumen of the connectable catheter. In some embodiments, the stylet may include, at a tip section thereof, an attachment member configured to attach to the connecting section of the indwelling stent end, such that when the stylet is proximally retracted within the inner lumen of the connectable catheter the indwelling stent is pulled into the inner lumen of the connectable catheter. In some embodiments, the stylet's attachment member may include a magnet configured to attract/approximate the connecting section of the indwelling stent. In some embodiments the stylet tip section may be bent to enable it to be attracted to the corresponding attachment members (such as magnets) of the connecting end of the indwelling stent, that are located below the stylet insertion path. In some embodiments, the attachment member (such as a magnet) is connected to the stylet tip flexibly to enable it to be attracted to magnets that are located behind the stylet insertion point out of the intermediary catheter tip and into the body cavity. In some embodiments, the stylet may be used for searching/locating the indwelling stent within the subject's body, without a need to visualize the indwelling stent. In some embodiments, the stylet may be used to attract, attach, connect and/or pull the indwelling stent into the inner lumen of the intermediary catheter. In some embodiments, the stylet tip section is integrally formed with the attachment member. In some embodiments, the attachment member of the stylet is attached or connected (temporary or permanently) to the tip section of the stylet. In some embodiments, the attachment member of the stylet is functionally associated with the tip section of the stylet. In some embodiments, the stylet's tip section (and/or the attachment member) is flexible and may bend in any direction, so as to allow the finding, attaching and/or connecting of the connection section of the indwelling stent within the subject's body. In some embodiments, the stylet tip section (and/or attachment member, if not integrally formed therewith) may be made of nitinol or other memory-material, which may acquire a bent or flexible shape when protruding through the tip section of the intermediary catheter. In some embodiments, the stylet may further be configured to provide an indication once a connection has been made to the connecting section of the indwelling stent. In some embodiments, the stylet's attachment member may include a loop, lasso, pigtail, net, basket structure or any combination thereof. In some embodiments, the connecting section of the indwelling stent is fitted with a corresponding connection member that may be as an integrated part of the stent luminal tube.

According to some embodiments, the connecting section of the indwelling stent may include a magnet or a component attractable by the stylet's magnet.

According to some embodiments, the stylet's attachment member may include a loop, lasso, pigtail, net, basket structure or any combination thereof, capable of attracting, attaching and/or connecting to the connecting section of the indwelling stent.

According to some embodiments, the stylet may further include or be functionally associated with an indication unit configured to provide an indication of a connection between the attachment member of the stylet and the connecting section of the indwelling stent. The indication may include any type of indication, such as, tactile indication, visual indication and/or audible indication.

According to some embodiments, the indwelling stent may further include a stopper element at an outer wall thereof, wherein the stopper element is located between the connecting section and the target section and wherein the stopper element is configured to determine the portion (length) of the indwelling stent that can enter the inner lumen of the connectable catheter. In some embodiments, the stopper includes a measured length of string connected between the stylet handle and a connector, fixed on the stylet, that fits an instillation port of the intermediary catheter. After the stylet is inserted into the intermediary catheter, the connector is closed/locked on the instillation port. After the stylet attachment member (for example, magnet) is attached/connected to the indwelling stent connecting section, the string is limiting the extent that the stylet can be pulled out of the temporary catheter, so that the coupled magnets are brought to the exact position, to ensuring sealing and securing thereof within the lumen of the intermediary catheter.

According to some embodiments, the connectable catheter system may further include a guide rod (such as a mandrel or guide wire) which may be removably insertable into the inner lumen of the connectable catheter. In some embodiments, the mandrel/guide wire may be configured to facilitate the penetration of the tip section of the connectable catheter into the body lumen.

According to some embodiments, the guide rod may be further configured to remove the indwelling stent from the connectable catheter when pushed distally within the inner lumen of the connectable catheter.

According to some embodiments, the intermediary catheter may further include a deployable anchoring element located at an outer wall thereof, the deployable anchoring element, when deployed, is configured to anchor the connectable catheter in the body lumen. In some embodiments, the deployable anchoring element is a balloon.

According to some embodiments, the intermediary catheter may further include one or more substance administration port(s)/connector(s) allowing the administration of the substance from the external section of the intermediary catheter to the target section of the indwelling stent.

According to some embodiments, the intermediary catheter may include more than one internal lumen. In some embodiments, the lumen(s) is configured to transfer fluids, substances or devices therethruought. In some exemplary embodiments, the intermediary catheter may include an additional internal lumen at a wall thereof. In some embodiments, an internal lumen may be as an inflation lumen, configured to inflate various internal members, such as, for example, but not limited to: securing member, sealing member, and the like. In some embodiments, the inner lumens may be parallel to each other and may be identical, similar or different in length, composition and/or diameter.

According to some embodiments, the system may further include a circuitry unit configured to provide various indications and/or controlling the operation of the system. In some embodiments, the control circuitry unit may be configured to provide indication when the respective ends of the intermediary catheter and the indwelling stent are attached/connected. In some embodiments, the control circuitry unit may be configured to provide indication when the continuous fluid passage is formed. In some embodiments, the circuitry unit is a control circuitry unit.

According to some embodiments, the system may further include a vacuum source configured to create a vacuum in the inner lumen of the connectable catheter to secure the positioning of the indwelling stent.

According to some embodiments, the system may further include means for heating and/or cooling a composition being instilled to the target cavity through the connectable catheter system, in order to control and vary the viscosity and other properties of the composition during instillation.

According to some embodiments, following completion of the instillation/administration of a desired material, the respective ends of the indwelling stent and the intermediary catheter can be disconnected. In an exemplary embodiment, the connecting section of the indwelling stent may have a smaller internal diameter than the tip section of intermediary catheter. Separating these two parts, after the connecting magnets are pushed out of the intermediary catheter, can be achieved by inserting a guide rod or stylet into the internal lumen, while exerting a force on the stopper of the indwelling stent. In a non-limiting example, this guide rod or stylet can have a known length, or visible scale of length, or an external string connected thereto, that ensure magnets separation, while reducing the risk of damage to the internal cavities, such as perforation of the internal cavity. In some embodiments, the separation of the connecting magnets can be achieved by an external magnet that is placed externally in close proximity to the internal cavity while detracting the magnet at the end of the indwelling stent, while the intermediary catheter is pulled away. In some embodiments, the magnets may have longitudinal polarization and thus rotating the intermediary catheter may cause the magnets to realign in a way that detracts them from one another.

After separation between the intermediate catheter and the indwelling stent, the intermediary catheter may be removed from the body. The indwelling stent is thus retained in its internal location after removal of the intermediary catheter, and can be used again in subsequent uses. With the indwelling stent maintained in position, subsequent uses (such as instillations) may be performed without the use of x-ray guidance and possibly with just mild sedation, thus reducing radiation hazards, insertion trauma and anesthesia complications. For example, retaining the indwelling stent inside the urinary tract for subsequent instillations tends to prevent or minimize infection, irritation, sensitization and injuries to the ureter orifice that may be incurred by repeated instillations of ureteral catheter in the upper urinary tract. The outer surface of the indwelling stent may be coated with a hydrogel to reduce friction between the indwelling stent and body tissues during insertion and during the indwelling period. Risk of infection may be reduced by application of an antibacterial coating to the outer surface of the indwelling stent.

According to some embodiments, the system may include the sequential or parallel use of more than one intermediary catheter and/or more than one indwelling stent. In some embodiments, an indwelling stent may be connected sequentially to one or more intermediary catheters, such that in one instance a substance is being delivered/administered from an external location to an internal body location and in a second instance, a substance is being removed from the internal location to an external location. For example, circulation of a substance may be performed whereby the substance is administered via a first continuous catheter system and is being removed via a second continuous catheter system. This may be utilized, for example, for inserting a heated substance to a target location and removing the heated substance from the internal target location, while performing circulation of said substance within the internal target location.

In some embodiments, more than one connectable continuous catheter systems may be used. In such a system, for example two or more indwelling stents (that may be identical, similar or different) may be connected to corresponding two or more internal lumens within the intermediary catheter. In such settings one or more stylets may be used. For example, one stylet may be used to attach and/or connect and/or attract a first indwelling stent and then the second indwelling stent. In some examples, two separate stylets may be used, each attaches to a separate indwelling catheter.

According to some embodiments, there is provided an intermediary (main) catheter, comprising: an external (proximal) section (end) and a tip (distal/internal) section (end), the tip section is configured to be inserted into a body lumen of a subject; a securing member located at an inner lumen of the intermediary (main) catheter, the securing member is configured to secure a connecting section of an indwelling stent within the inner lumen of the tip section region thereof and thereby to form a continuous fluid passage (conduit) between the inner lumen of the connectable catheter and an inner lumen of the indwelling stent. In some embodiments, the securing member may be further configured to seal a fluid passage between an outer wall of the reconnectable indwelling stent and the inner wall of the intermediary catheter. In some embodiments, the intermediary catheter may further include a sealing member configured to seal a fluid passage between the outer wall of the reconnectable indwelling stent and the inner wall of the intermediary catheter.

According to some embodiments, there is provided an indwelling stent, comprising: a connecting section and a target section, the target section is configured to be positioned into a target body cavity of a subject; the connecting section is configured to reversibly connect, within a body lumen, to the tip section of an intermediary catheter; and a stopper element at an outer wall thereof, wherein the stopper element is located between the connecting section and the target section and wherein the stopper element is configured to determine the portion (length) of the indwelling stent that can enter an inner lumen of the intermediary catheter.

In some embodiments, the indwelling stent, and/or the intermediary catheter may be made of medical grade biocompatible polymers that are resistant to aging, histocompatible, non-toxic and have smooth facials. One or both of the indwelling stent, and the intermediary catheter may be disposable or suitable for multiple uses.

According to some embodiments, the indwelling stent may further include X-ray markers at its tip section (radioopaque lines) for fluoroscopy visualization.

In some embodiments, the indwelling stent may include one or more anchors, located at the target section, which allow the positioning and securing of the target section of indwelling stent in the target cavity. For example, one or more anchors formed from a shape memory alloy may be used to anchor the indwelling stent.

According to some embodiments, the system of the invention may be provided with means for generating an indication that the respective ends of the indwelling stent and the intermediary catheter are connected in a fluid-tight connection. For example, electrical contacts may be present at the tip section of the intermediary catheter internal lumen, which may form a closed circuit when a connection is formed. Closure of the contacts creates an electric current in a circuit which can be used as an indication that the fluid-tight connection has been formed. In another embodiment, a thin tube which conducts air as part of the internal lumen of the intermediary catheter may be used. In such embodiment, the tube path is designed so that the air pressure inside the tube is affected by the connection between the indwelling stent and the intermediary catheter. Changes in the tube internal air pressure indicate the formation of a connection and a level can be defined for indication of a fluid-tight connection. Additionally or alternatively, the pressure inside the locking balloon (as shown in FIG. 1) can be monitored and a predetermined pressure level can serve as indication that the attachment means (for example, magnets), are locked in position inside the lumen of the intermediary catheter.

In some embodiments, the locking of the connecting members (for example, magnets) can be achieved by a locking mechanism that is either designed as part of the internal lumens or is inserted through the intermediary catheter lumen and pulled against a distal magnet, thus creating a lock mechanism that requires no external indication to verify its integrity.

According to some embodiments, there is provided a method of connecting a connectable catheter system, the method comprising: attaching and/or drawing a connecting section of an indwelling stent into an inner lumen of the intermediary catheter; securing the connecting section of the indwelling stent within the inner lumen of the tip section of connectable catheter thereby forming a continuous fluid passage between the inner lumen of the connectable catheter and an inner lumen of the indwelling stent; and utilizing a control circuitry unit, providing an indication when the continuous fluid passage is formed.

According to some embodiments, the process of connecting the connecting section of the indwelling stent and the tip section of intermediary catheter (both ends reside in the subjects body) may comprise the steps of (i) seeking the connecting section of the indwelling stent, (ii) drawing the connecting section of the indwelling stent towards the tip section of the intermediary catheter, (iii) connecting the respective ends of the indwelling stent and the intermediary catheter, (iv) securing the respective ends of the indwelling stent and the intermediary catheter together, and (v) confirming the secure attachment by an indication of the secure attachment. The connection process may be performed with or without the use of vision guidance.

Figure 7:
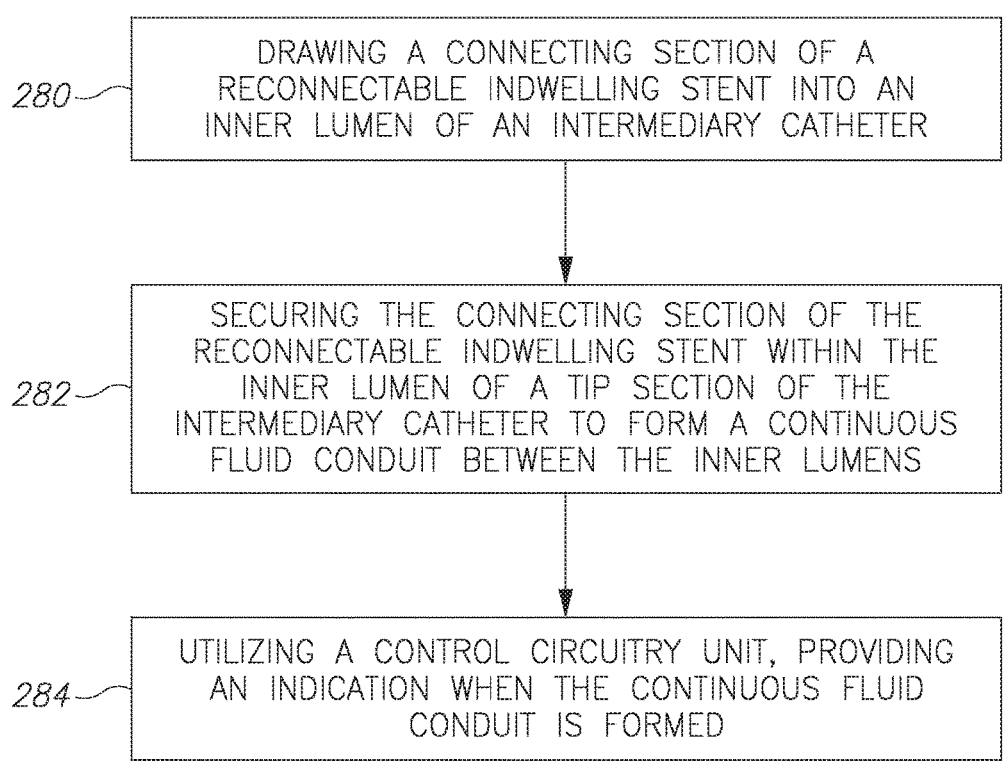
FIG. 7—a flow chart diagram showing steps in a method of connecting a connectable catheter system, according to some embodiments.

Reference is now made to FIG. 7, which is a block diagram of a method of connecting a connectable catheter system, according to some embodiments. As shown in FIG. 7, at step 280, a connecting section of the indwelling stent (located within the subject body) is drawn into the inner lumen of the intermediary catheter. Next, at step 282, the connecting section of the indwelling stent is secured within the inner lumen of a tip section of the intermediary catheter, while sealing the connection, to form a continuous fluid conduit between the inner lumens of the intermediary catheter and the intermediary catheter. At step 284, a control circuitry unit is utilized, to provide an indication when the continuous fluid conduit is formed, to allow the use of the connectable catheter system for the transfer of fluids and other materials to and from an external body location to an internal body location.

In some embodiments, securing the connecting section of the indwelling stent within the inner lumen of the tip section of connectable catheter includes deploying a securing member located at an inner lumen of the connectable catheter.

In some embodiments, drawing a connecting section of an indwelling stent into an inner lumen of the connectable catheter is conducted by inserting a stylet into the inner lumen of the connectable catheter, the stylet comprises, at a tip section thereof, an attachment member configured to attach to the connecting section of the catheter and, such that when the stylet is proximally retracted within the inner lumen of the connectable catheter, the indwelling stent is pulled into the inner lumen of the connectable catheter.

In some embodiments, the method may further include automatically providing, utilizing an indication unit, an indication when a connection between the attachment member of the stylet and the connecting section of the indwelling stent is formed.

According to some embodiments, once a fluid-tight connection (conduit) has been formed between the respective ends of the indwelling stent and the intermediary catheter, a material of choice (such as, but not limited to, a medication or other composition) that is to be instilled via the continuous catheter thus formed, may be attached to a connector at the external section of the intermediary catheter. For example, the medication or composition may be in contained in a syringe which is attached to a respective connector.

The material to be instilled into the target organ/cavity may be delivered in any formulation or compositions and may include various active or non-active ingredients, depending on the target organ and the required treatment regime. In some embodiments, the composition of choice may be delivered in the form of a gel that solidifies in the body and slowly releases the drug over a period of time, such as several hours. In some exemplary embodiments, the medicated gel has a low viscosity at below body temperature and high viscosity at body temperature. Such a gel can be instilled, for example, into the upper urinary tract in its fluid state and then become very viscous as its temperature rises to body temperature in the upper urinary tract. Using this type of gel enables the filling of essentially the entire volume of the upper tract (or any target cavity to be treated), including difficult to reach areas, such as renal calyces and the complete length of the ureter.

In some non-limiting examples, liquid medication, for example chemotherapy mixed with water for injection may be instilled into the target organ. In some exemplary embodiments, the medication is mitomycin C.

In another non-limiting example, liquid medication, for example chemotherapy mixed with water for injection is instilled into the renal pelvis while fluids are extracted from bladder. In a non-limiting example, the rate of instillation and extraction are similar to form a close circulation of medication throughout the urinary tract. In a non-limiting example, a heater may be integrated into the medication closed circulation to provide heated medication into the urinary tract.

It is possible to use the connection to the indwelling stent to introduce medications to address potential adverse effects that are known to effect indwelling stents. Such medication can include pain-relief (such as lidocaine), infection drugs (such as antibiotics) and similar. This capability enhances the safety and reduces medical risks of indwelling stents of the present invention.

According to some embodiments, the systems, devices and method disclosed herein may be used for administration of various substances to various internal target organs, while minimizing risks associated therewith (such as radiation hazards, insertion trauma, anesthesia complications, infections, irritation, sensitizations, injuries, and the like.).

According to some embodiments, the systems and methods disclosed herein may be used for the treatment of various conditions.

In some embodiments, there is provided a method of treating cancer. In some embodiments, the cancer is urinary tract cancer. In some embodiments, the cancer is bladder cancer. In some embodiments, the cancer is kidney cancer. In some embodiments, the cancer is urethral cancer. In some embodiments, the cancer is a body cavity cancer.

In some embodiments, the system may be used to provide a medication to a target organ, in order to treat a condition, such as cancer.

In some embodiments, the target organ may be selected from, but not limited to: stomach, bladder, kidney, heart, intestines, uterus, lungs, urinary tract, and the like, or combinations thereof. Each possibility is a separate embodiment.

In some exemplary embodiments, the system disclosed herein may be used for instillation of composition to the urinary tract.

Figures 8A, 8B:
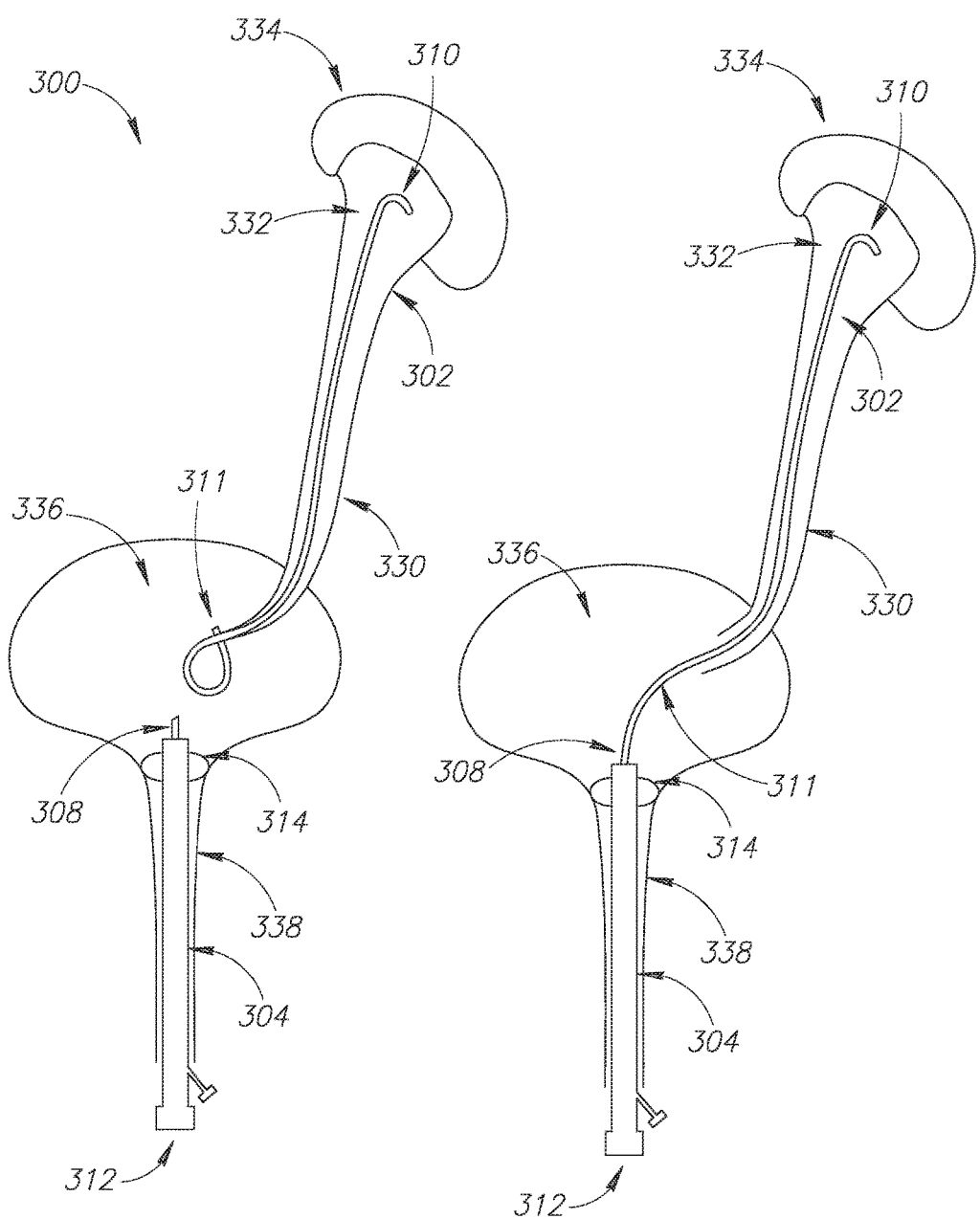
FIGS. 8A-B show an exemplary use of the connectable catheter system after positioning in a urinary tract prior to (FIG. 8A) or after (FIG. 8B) attachment of the indwelling stent to the intermediary catheter.

Reference is now made to FIGS. 8A-B, which show a catheter system (300) after being positioned in a urinary tract. Shown in FIG. 8A is indwelling stent (302) after being positioned in a ureter (330) of a male or female subject. The target section (310) of indwelling stent (302) is positioned in renal pelvis (332) of a kidney (334). The connecting section (311) of indwelling stent (302) is positioned in the urinary bladder (336) of the subject. The target section (310) of the indwelling stent (302) may be able to coil into a "pigtail" or "double pigtail", in order to anchor the target section (310) of indwelling stent (302) in the renal pelvis (332) and prevent migration from the renal pelvis (332) downwards or upwards. The indwelling stent (302) may comprise one or more anchors to prevent migration thereof. The intermediary catheter (304) is adapted/configured to be inserted through the meatus into the urethra until the tip section (308) is located inside bladder (336). As shown, intermediary catheter (304) is positioned in a urethra (338) of the subject with the tip section (308) being positioned in bladder (336), and the external section (312) of the being positioned outside the body. After inflation of anchoring balloon (314) inside bladder (336), the intermediary catheter (304) may be pulled, such that anchoring balloon (314) is located in the neck region of bladder (336). The tip section (308) of the intermediary catheter (304) is configured to reversibly connect to the connecting section (311) of indwelling stent (302) inside bladder (336), as shown in FIG. 8B. When connected, the indwelling stent (302) and the intermediate catheter (304) form a continuous channel from outside the body to the renal pelvis (332, target organ). As detailed above, approximation of the respective ends of the intermediary catheter and indwelling stents inside the bladder may be facilitated by various means, such as, use of magnets (for example, hollow cylindrical magnetic tips of opposite polarities, external magnets, and the like). For example, in some cases, when the bladder sags and the connecting section of the indwelling stent is located further from the meatus, it may be beneficial to bring the ends to closer proximity before the intermediary catheter scanning. This may be achieved, for example, by a magnet that is manipulated outside of the body together with magnetic or magnetizable particles on the respective tips of the respective catheters to bring the ends together. In some embodiments, the external magnet will be radially polarized so as to attract both magnet polarities.

When the respective ends of both the indwelling stent and the intermediary catheter are present/located in the bladder (as demonstrated in FIG. 8A), the ends may attract each other by the magnetic field and spontaneously form a stable, fluid tight connection between them (as demonstrated in FIG. 8B). As detailed above, means may be provided to ensure an end to end attachment of the components and prevent a side by side attachment.

According to some exemplary embodiments, when used in the urethra system, the outer diameter of the indwelling stent may be for example, 6 F from the target (renal) end and all along the part that is deployed in the ureter. This would allow the indwelling stent to be inserted, as a non-limiting example, over, a 0.038"guide wire. The indwelling stent may be flared at its bladder end so as to terminate at the bladder end with an outer diameter, for example, of 16 F. In some embodiments, the opening of the indwelling stent at the target section may allow instillation of a high viscosity gel to the renal pelvis.

According to some embodiments, the size and diameter of the indwelling stents and/or the intermediary catheter may vary according to the target organ and the internal location thereof. In some exemplary embodiments, the indwelling catheter may have a length of about 35-40 cm (for a male subject), and about 25-30 cm (for a female subject). For example, the indwelling stent may have a length of about 26-34 cm (for Male or Female subjects), and about 20-24 cm (pediatrics). For example, a guide rod (for example, a mandrel) may have a length of 40-45 cm (for male), and 30-35 cm for female. For example, the stylet may be at a length of about 40-50 cm.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

What is claimed is:

1. A connectable catheter system, comprising:
an intermediary catheter comprising an external section and a tip section, the tip section is configured to be inserted into a body of a subject;
a reconnectable indwelling stent comprising a connecting section and a target section, the target section being configured to be located within a body of the subject, and
a stylet removably insertable into the inner lumen of the intermediary catheter,
wherein the connecting section of the reconnectable indwelling stent is configured to reversibly connect, within the body of the subject, to the tip section of the intermediary catheter to form a continuous conduit between the intermediary catheter and the reconnectable indwelling stent, and
wherein the stylet comprises, at a tip section thereof, an attachment member configured to attach to the connecting section of the reconnectable indwelling stent, such that when the stylet is attached to the reconnectable indwelling stent and is proximally retracted within the inner lumen of the intermediary catheter, the reconnectable indwelling stent is pulled into the inner lumen of the intermediary catheter.

2. The connectable catheter system of claim 1, wherein the connecting section of the reconnectable indwelling stent is configured to fit into an inner lumen of the tip section of the intermediary catheter; wherein the inner lumen of the intermediary catheter comprises a securing member configured to secure the connecting section of the reconnectable indwelling stent within the inner lumen of the tip section of the intermediary catheter; and wherein the securing member is further configured to seal a fluid passage between the outer wall of the reconnectable indwelling stent and the inner wall of the intermediary catheter.

3. The connectable catheter system of claim 2, wherein the securing member comprises a deployable securing member, vacuum ducts, flexible plate, matching recesses in the connecting section of the reconnectable indwelling stent and the inner lumen of the tip section of the intermediary catheter, or any combination thereof.

4. The connectable catheter system of claim 2, wherein the securing member comprises one or more inflatable balloons, configured to be inflated within the inner lumen of the intermediary catheter, and wherein the intermediary catheter further comprises an inflating port configured to inflate the one or more inflatable balloons.

5. The connectable catheter system of claim 1, wherein the intermediary catheter further comprises a sealing member configured to seal a fluid passage between the outer wall of the reconnectable indwelling stent and the inner wall of the intermediary catheter.

6. The connectable catheter system of claim 1, wherein the stylet's attachment member comprises a magnet configured to attract the connecting section of the reconnectable indwelling stent, and wherein the connecting section of the reconnectable indwelling stent comprises a magnet or a component attractable by the stylet's magnet.

7. The connectable catheter system of claim 1, wherein the stylet further comprises or is functionally associated with an indication unit configured to provide an indication of a connection between the attachment member of the stylet and the connecting section of the reconnectable indwelling stent.

8. The connectable catheter system of claim 2, wherein the reconnectable indwelling stent comprises a stopper element at an outer wall thereof, wherein the stopper element is located between the connecting section and the target section and wherein the stopper element is configured to limit the length of the reconnectable indwelling stent that can enter the inner lumen of the intermediary catheter.

9. The connectable catheter system of claim 1, further comprising a guide rod removably insertable into the inner lumen of the connectable catheter, the guide rod is configured to facilitate the penetration of the tip section of the intermediary catheter into the subject's body and to remove the reconnectable indwelling stent from the intermediary catheter when pushed distally within the inner lumen of the connectable catheter.

10. The connectable catheter system of claim 1, further comprises a circuitry unit configured to provide an indication when the continuous fluid conduit is formed.

11. The connectable catheter system of claim 1, further comprises a vacuum source configured to create vacuum in the inner lumen of the intermediary catheter to secure the positioning of the reconnectable indwelling stent.

* * * * *